(12) United States Patent
Del Valle

(10) Patent No.: US 10,507,226 B1
(45) Date of Patent: Dec. 17, 2019

(54) N-AMINO PEPTIDE BETA-SHEET MIMICS FOR THE TREATMENT OF ALZHEIMER'S DISEASE

(71) Applicant: Juan R. Del Valle, Tampa, FL (US)

(72) Inventor: Juan R. Del Valle, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/231,086

(22) Filed: Dec. 21, 2018

Related U.S. Application Data

(60) Provisional application No. 62/665,910, filed on May 2, 2018.

(51) Int. Cl.
*A61K 38/02* (2006.01)
*C07K 7/02* (2006.01)
*A61P 25/28* (2006.01)

(52) U.S. Cl.
CPC .............. *A61K 38/02* (2013.01); *A61P 25/28* (2018.01); *C07K 7/02* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,880,635 A | 11/1989 | Janoff et al. | |
| 4,906,477 A | 3/1990 | Kurono et al. | |
| 4,911,928 A | 3/1990 | Wallach | |
| 4,917,951 A | 4/1990 | Wallach | |
| 4,920,016 A | 4/1990 | Allen et al. | |
| 4,921,757 A | 5/1990 | Wheatley et al. | |
| 7,060,670 B1 * | 6/2006 | Chalifour | A61K 38/08 514/15.4 |
| 10,351,602 B1 * | 7/2019 | Del Valle | C07K 7/66 |
| 2005/0090439 A1 * | 4/2005 | Chalifour | A61K 39/0007 424/185.1 |
| 2013/0164219 A1 | 6/2013 | Brinkmann et al. | |

OTHER PUBLICATIONS

Thermo, 2004. N-terminal acetylation and C-terminal Amidation of Peptides. (Year: 2004).*
Cheng et al., "Amyloid β-Sheet Mimics that Antagonize Amyloid Aggregation and Reduce Amyloid Toxicity," Nat Chem, 2012, 4(11): 927-933.
DiChiara et al., "Alzheimer's toxic amyloid beta oligomers: Unwelcome visitors to the Na/K ATPase alpha3 docking station," Yale Journal of Biology and Medicine, 2017, 90, 45-61.
Gordon et al., "Inhibition of β-Amyloid(40) Fibrillogenesis and Disassembly of β-Amyloid(40) Fibrils by Short β-Amyloid Congeners Containing N-Methyl Amino Acids at Alternate Residues," Biochemistry, 2001, 40(28): 8237-8245.
Heagerty et al., "Time-dependent ROC curves for censored survival data and a diagnostic marker," Biometrics, 2000, 56(2):337-344.
IUPAC 1974 Recommendations for Section E, Fundamental Stereochemistry, in Pure Appl. Chem., 1976, 45: 13-30.
Kang et al., "Access to Enantiopure α-Hydrazino Acids for N-Amino Peptide Synthesis," J. Org. Chem., 2017, 82, 1833-1841.
Kokkoni et al., "N-Methylated Peptide Inhibitors of β-Amyloid Aggregation and Toxicity. Optimization of the Inhibitor Structure," Biochemistry 2006, 45(32): 9906-9918.
Kyte et al., "A Simple Method for Displaying the Hydropathic Character of a Protein," J. Mol. Biol. 1982, 157, 105-132.
Müller et al., "Not just amyloid: physiological functions of the amyloid precursor protein family," Nat. Rev. Neur., 2017, 18(5): 281-298.
Sarnowski et al., "Peptide N-Animation Supports β-Sheet Conformations," Journal of the Gesellschaft Deutscher Chemiker, 2017, 56, 2083-2086.
Sarnowski et al., "Synthesis and β-Sheet Propensity of Constrained N-amino Peptides," Bioorganic & Medicinal Chemistry, 2018, 26, 1162-1166.

\* cited by examiner

*Primary Examiner* — Marcela M Cordero Garcia
(74) *Attorney, Agent, or Firm* — Meunier Carlin & Curfman LLC

(57) ABSTRACT

Disclosed herein are compounds comprising short N-aminated peptides and compositions comprising the same. The disclosed compounds and compositions maybe used in methods of inhibiting amyloid-beta aggregation and treating Alzheimer's disease.

14 Claims, 19 Drawing Sheets

DH04

EA04

DH08

EE01

DH09

DH07

DH05

EA07

EA01

EA05

EA03

EA02

DH06

EA09

N-AMINO PEPTIDE BETA-SHEET MIMICS FOR THE TREATMENT OF ALZHEIMER'S DISEASE

CROSS-REFERENCE TO RELATED APPLICATIONS

This application claims priority to U.S. Provisional Patent Application No. 62/665,910, filed May 2, 2018, which is incorporated herein by reference in its entirety.

STATEMENT REGARDING FEDERALLY SPONSORED RESEARCH

This invention was made with government support under grant CH1709927 awarded by the National Science Foundation. The government has certain rights in the invention.

TECHNICAL FIELD

The present disclosure relates to the synthesis and development of short N-aminated peptides and methods of using the same for the treatment of Alzheimer's disease.

INTRODUCTION

Alzheimer's disease (AD) is a rapidly progressive neurodegenerative disease that affects over 5 million people in the United States alone. Although treatments may help relieve some of the physical or mental symptoms associated with AD, there is currently no cure or way to slow disease progression. As such, there is a critical need for new and effective therapies to treat AD.

SUMMARY

In one aspect, disclosed are compounds of formula (I),

Further disclosed herein are compositions comprising the compounds, methods of reducing or inhibiting amyloid-beta aggregation in a subject using the compounds and compositions as detailed herein, and methods of treating Alzheimer's disease in a subject using the compounds and compositions as detailed herein.

Other aspects and embodiments of the disclosure will become apparent in light of the following description and drawings.

BRIEF DESCRIPTION OF THE DRAWINGS

FIG. 1A shows representative mono-aminated peptides of formula (I). FIG. 1B shows representative di-aminated peptides of formula (I). FIG. 1C shows representative tri-aminated peptides of formula (I).

DETAILED DESCRIPTION

Figure 1A:
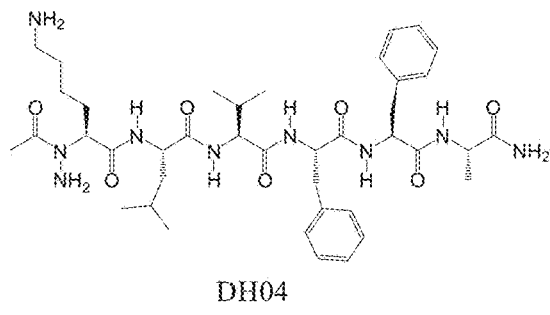
FIGS. 1A-1C show representative compounds of formula (I).
Figure 1A:
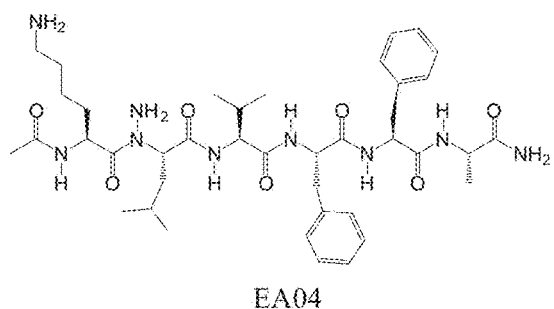
Figure 1A:
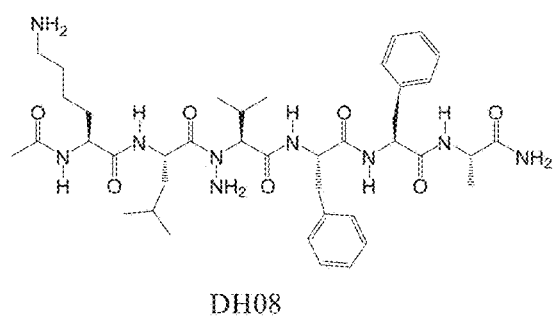
Figure 1A:
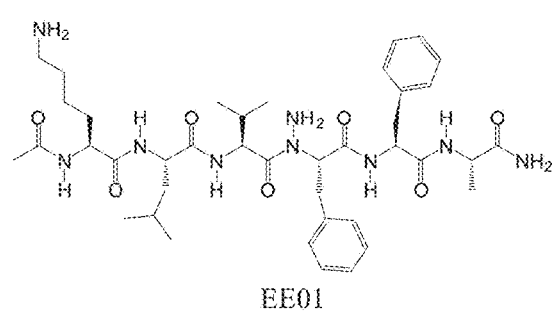
Figure 1A:
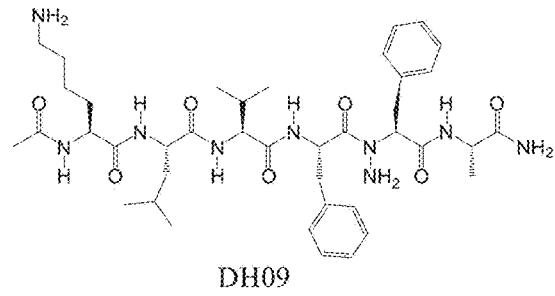
Figure 1A:
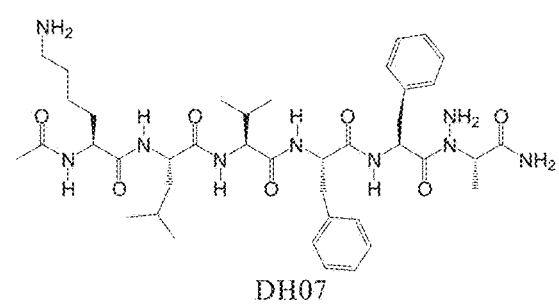
Figure 1B:
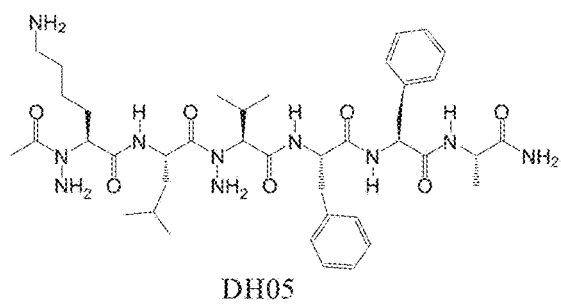
Figure 1B:
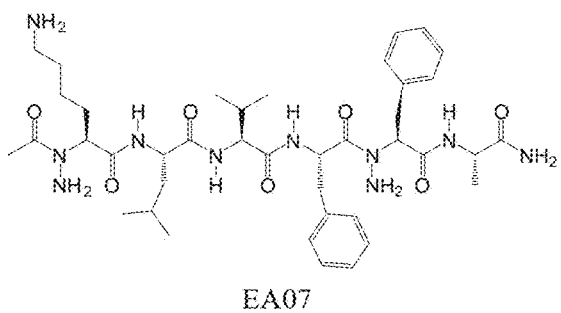
Figure 1B:
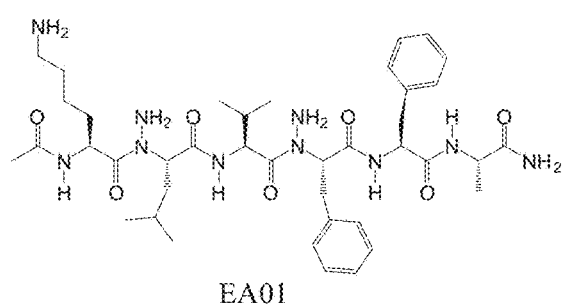
Figure 1B:
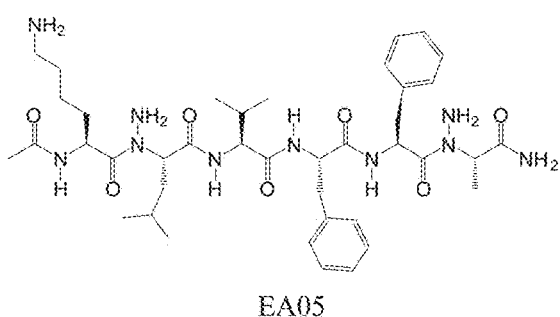
Figure 1B:
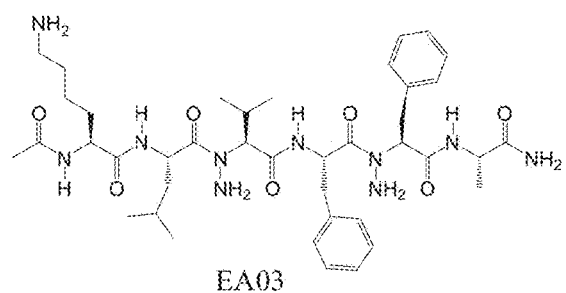
Figure 1B:
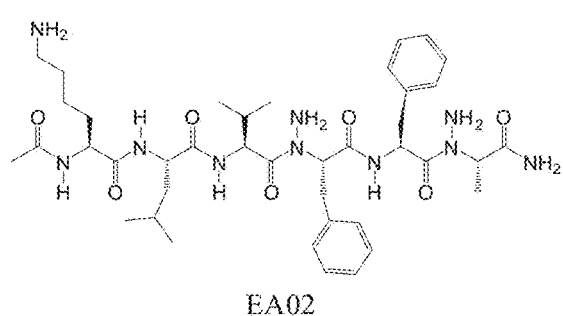
Figure 1C:
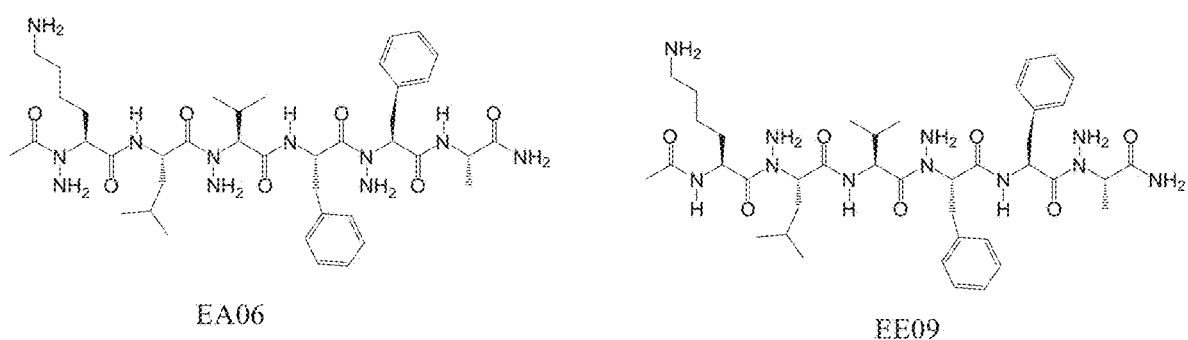
Figure 1D:
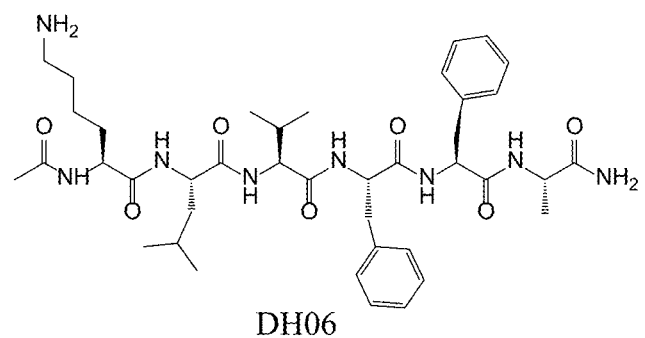
FIG. 1D shows other aminated peptides.
Figure 1D:
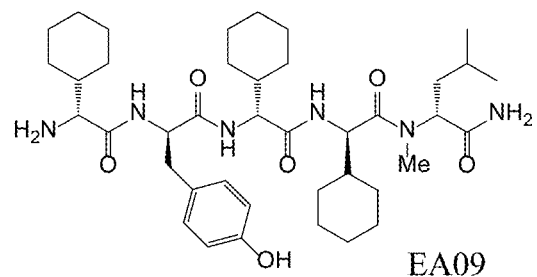

Described herein are compounds that reduce or inhibit aggregation of amyloid-beta. Accordingly, the compounds as described herein may be used to treat Alzheimer's disease.

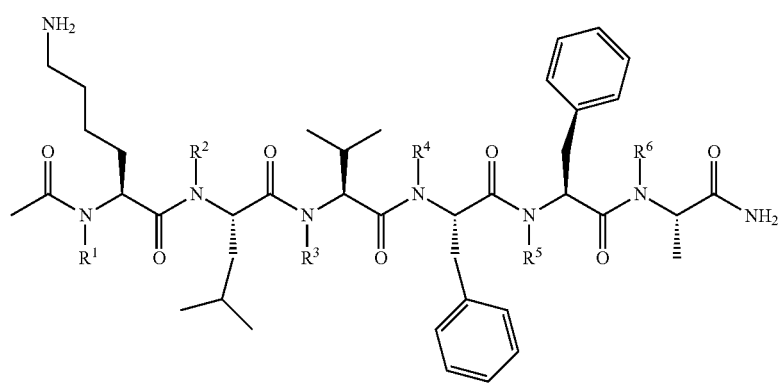

(I)

or a pharmaceutically acceptable salt thereof, wherein $R^1$, $R^2$, $R^3$, $R^4$, $R^5$, and $R^6$ are each independently selected from hydrogen or —$NH_2$.

In some embodiments, at least one of $R^1$, $R^2$, $R^3$, $R^4$, $R^5$, and $R^6$ is —$NH_2$. In some embodiments, two of $R^1$, $R^2$, $R^3$, $R^4$, $R^5$, and $R^6$ is —$NH_2$. In some embodiments, three of $R^1$, $R^2$, $R^3$, $R^4$, $R^5$, and $R^6$ is —$NH_2$. In some embodiments, $R^1$ and $R^3$ are —$NH_2$, $R^1$ and $R^5$ are —$NH_2$, $R^2$ and $R^4$ are —$NH_2$, $R^2$ and $R^6$ are —$NH_2$, $R^3$ and $R^5$ are —$NH_2$, $R^4$ and $R^6$ are —$NH_2$, $R^1$, $R^3$, and $R^5$ are —$NH_2$, or $R^2$, $R^4$ and $R^6$ are —$NH_2$.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "agonist" refers to a molecule or compound that triggers (e.g., initiates or promotes), partially or fully enhances, stimulates, or activates one or more biological activities. An agonist may mimic the action of a naturally occurring substance. Whereas an agonist causes an action, an antagonist blocks the action of the agonist.

The term "amination" as used herein refers to the process in which an amino group is added to a molecule. For example, when a bond is formed between a nitrogen atom in the molecule and the amino group the molecule is "N-aminated." Amination can occur in a number of ways including reaction with ammonia or another amine such as in an alkylation, reductive amination, electrophilic amination and the Mannich reaction or enzymatically by aminases.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "amyloid-beta", "amyloid beta", "A-beta", "Abeta", or "Aβ" as used interchangeably herein refers to a peptide of from 36 to 43 amino acids that is found in the brain. Amyloid-beta is formed after sequential cleavage of the amyloid precursor protein (APP), a transmembrane glycoprotein, by the β- and γ-secretases. The most common isoforms of the amyloid-beta peptide are 40 amino acids in length (Aβ40) and 42 amino acids in length (Aβ42). The Aβ40 form is the more common of the two forms, but Aβ42 may be more fibrillogenic. Aggregation of amyloid-beta may lead to Alzheimer's disease.

The term "antagonist" or "inhibitor" refers to a molecule which blocks (e.g., reduces or prevents) a biological activity.

As used herein, the term "agonist" refers to a molecule or compound that triggers (e.g., initiates or promotes), partially or fully enhances, stimulates, or activates one or more biological activities. An agonist may mimic the action of a naturally occurring substance. Whereas an agonist causes an action, an antagonist blocks the action of the agonist.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "composition", "compositions", "pharmaceutical composition", and "pharmaceutical compositions" are used interchangeably herein to refer to a composition comprising the disclosed compounds.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be an subject or cell without a compound as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

A "pharmaceutically acceptable excipient," "pharmaceutically acceptable diluent," "pharmaceutically acceptable carrier," or "pharmaceutically acceptable adjuvant" as used interchangeably herein means an excipient, diluent, carrier, and/or adjuvant that is useful in preparing a pharmaceutical composition that is generally safe, non-toxic, and neither biologically nor otherwise undesirable, and includes an excipient, diluent, carrier, and adjuvant that is acceptable for veterinary use and/or human pharmaceutical use, such as those promulgated by the United States Food and Drug Administration.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target or activity is to be detected or determined or any sample comprising a compound as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" and "patient" as used interchangeably herein can mean a mammal that wants or is in need of the herein described compounds. The subject may be a human or a non-human animal. The subject may be a vertebrate. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. In some embodiments, the subject is human. The subject may be of any age or stage of development, such as, for example, an adult, an adolescent, or an infant. In some embodiments, the subject has a specific genetic marker. The subject may be diagnosed with or at risk of developing Alzheimer's disease. The subject or patient may be undergoing other forms of treatment.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides.

A "therapeutically effective amount" or "effective amount" as used interchangeably herein is an amount sufficient to elicit a therapeutic effect. Amounts effective for this use will depend on, e.g., the particular composition of the regimen administered, the manner of administration, the stage and severity of the disease, the general state of health of the subject, and the judgment of the prescribing physician. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically effective amount may be administered in one or more administrations (e.g., the composition may be given as a preventative treatment or therapeutically at any stage of disease progression, before or after symptoms, and the like), applications or dosages and is not intended to be limited to a particular formulation, combination or administration route. It is within the scope of the present disclosure that the disclosed compositions may be administered at various times during the course of treatment of the subject. The times of administration and dosages used will depend on several factors, such as the goal of treatment (e.g., treating v. preventing), condition of the subject, etc. and can be readily determined by one skilled in the art. Administration may be adjusted according to individual need and professional judgment of a person administrating or supervising the administration of the compounds used in the present invention.

"Toxic" refers to a substance causing any adverse effect when administered to a subject. The term "non-toxic" refers to a substance that has a relatively low degree to which it can damage a subject. Toxicity can refer to the effect on a whole organism, such as an animal, bacterium, plant, or other subject as defined herein, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. A composition or compound that is relatively non-toxic may allow a wider range of subjects to be able to safely handle the composition or compound, without serious safety concerns or risks.

"Treat," "treatment," or "treating," when referring to protection of a subject from a disease or infection means suppressing, repressing, ameliorating, or completely eliminating the disease or infection. Preventing the disease or infection involves administering a compound or composition of the present invention to a subject prior to onset of the disease or infection. Suppressing the disease or infection involves administering a compound or composition of the present invention to a subject after induction of the disease or infection but before its clinical appearance. Repressing or ameliorating the disease or infection involves administering a compound or composition of the present invention to a subject after clinical appearance of the disease or infection.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of*

*Organic Synthesis*, 3rd Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkynyl" as used herein, means an unsaturated hydrocarbon chain containing from 2 to 20 carbon atoms and at least one carbon-carbon triple bond.

The term "alkoxyalkyl," as used herein, refers to an alkoxy group, as defined herein, appended to the parent molecular moiety through an alkylene group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl group, or a bicyclic or tricyclic fused ring system. Bicyclic fused ring systems are exemplified by a phenyl group appended to the parent molecular moiety and fused to a phenyl group, a cycloalkyl group as defined herein, a heteroaryl group as defined herein, or a heterocycle as defined herein. Tricyclic fused ring systems are exemplified by a phenyl group appended to the parent molecular moiety and fused to a bicyclic fused ring system as described herein. Representative examples of aryl include, but are not limited to, phenyl, naphthyl, anthracenyl, indolyl (e.g., 1H-indol-4-yl, 1H-indol-5-yl, 1H-indol-6-yl, and 1H-indol-7-yl), benzodioxolyl (e.g., benzo[d][1,3]dioxol-4-yl and benzo[d][1,3]dioxol-5-yl), chromanyl (e.g., chroman-5-yl, chroman-6-yl, chroman-7-yl, and chroman-8-yl), quinolinyl, and tetrahydroquinolinyl (e.g., 1,2,3,4-tetrahydroquinolin-5-yl, 1,2,3,4-tetrahydroquinolin-6-yl, 1,2,3,4-tetrahydroquinolin-7-yl, and 1,2,3,4-tetrahydroquinolin-8-yl).

The term "arylalkyl" as used herein, refers to an aryl group, as defined herein, appended to the parent molecular moiety through an alkylene group, as defined herein.

The term "carboxyl" as used herein, means a carboxylic acid, or —COOH.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. The cycloalkyl may be monocyclic, bicyclic, bridged, fused, or spirocyclic. Monocyclic cycloalkyl groups contain 3 to 10 carbon atoms, preferably 4 to 7 carbon atoms, and more preferably 5 to 6 carbon atoms in the ring. Bicyclic cycloalkyl groups contain 8 to 12 carbon atoms, preferably 9 to 10 carbon atoms in the ring. Cycloalkyl groups may be substituted or unsubstituted. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "cycloalkynyl," as used herein, means a monocyclic or multicyclic ring system containing at least one carbon-carbon triple bond and preferably having from 5-10 carbon atoms per ring or more than 10 carbon atoms per ring.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P, and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O, and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic" or "heterocyclyl" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N, and S. The six-membered ring contains zero, one or two double bonds and one, two, or three heteroatoms selected from the group consisting of O, N, and S. The seven- and eight-membered rings contains zero, one, or two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-di hydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocyclylalkyl" as used herein, refers to a heterocycle group, as defined herein, appended to the parent molecular moiety through an alkylene group, as defined herein.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "═══" designates a single bond (—) or a double bond (═).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

When substituent groups are specified by their conventional chemical formulae, written from left to right, such a formula also encompasses the same substituent that would result from writing the structure from right to left. For example, —CH$_2$NH— is also intended to encompass —NHCH$_2$—.

2. COMPOUNDS

In one aspect, disclosed is a compound of formula (I),

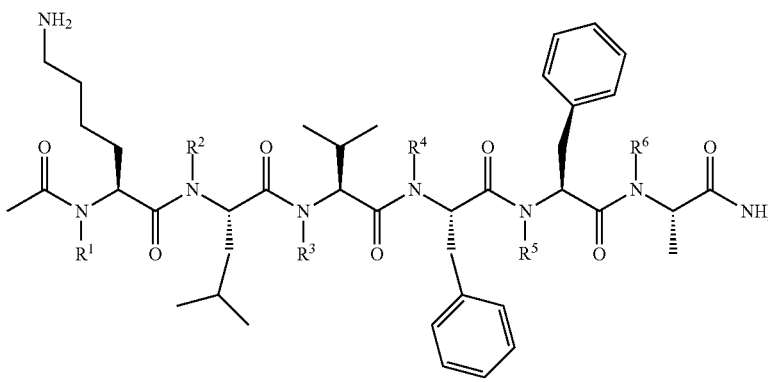

(I)

or a pharmaceutically acceptable salt thereof, wherein R$^1$, R$^2$, R$^3$, R$^4$, R$^5$, and R$^6$ are each independently selected from hydrogen or —NH$_2$.

In some embodiments, at least one of R$^1$, R$^2$, R$^3$, R$^4$, R$^5$, and R$^6$ is —NH$_2$. In some embodiments, two of R$^1$, R$^2$, R$^3$, R$^4$, R$^5$, and R$^6$ is —NH$_2$. In some embodiments, three of R$^1$, R$^2$, R$^3$, R$^4$, R$^5$, and R$^6$ is —NH$_2$. In some embodiments, Wand R$^3$ are —NH$_2$, Wand R$^5$ are —NH$_2$, R$^2$ and R$^4$ are —NH$_2$, R$^2$ and R$^6$ are —NH$_2$, R$^3$ and R$^5$ are —NH$_2$, R$^4$ and R$^6$ are —NH$_2$, R$^1$, R$^3$ and R$^5$ are —NH$_2$, or R$^2$, R$^4$ and R$^6$ are —NH$_2$. Examples of compounds of formula (I) are shown in FIG. 1A-FIG. 1D. In some embodiments, the compound comprises a mono-aminated peptide. Mono-aminated peptides may include, for example, DH04, EA04, DH08, EE01, DH09, and DH07. In some embodiments, the compound comprises a di-aminated peptide. Di-aminated peptides may include, for example, DH05, EA07, EA01, EA05, EA03, and EA02. In some embodiments, the compound comprises a tri-aminated peptide. Tri-aminated peptides may include, for example, EA06 and EE09. In some embodiments, the compound comprises DH04, DH05, DH06, DH07, DH08, DH09, EA01, EA02, EA03, EA04, EA05, EA06, EA07, EE01, EE09, or EA09, or a combination thereof. In some embodiments, the compound comprises DH04, DH05, DH07, DH08, DH09, EA01, EA02, EA03, EA04, EA05, EA06, EA07, EE01, or EE09, or a combination thereof. In some embodiments, the compound does not comprise DH06 or EA09.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated are $^{11}$C, $^{13}$N, $^{15}$O, and $^{18}$F. Isotopically-labeled compounds can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

N-amino peptides which retain their normal Cα substituents are constrained by both covalent and noncovalent interactions, which results in a reduction of the number of accessible torsion bond angles. In contrast to oligomeric N-alkylated peptides, the N-amino substituent in the N-amino peptides described herein offer additional sites for hydrogen bonding or subsequent chemical diversification.

Abbreviations used in the Schemes and descriptions that follow include the following: AA is amino acid; Boc is tert-butyloxycarbonyl; DCM is dichloromethane; DIEA is N, N-Diisopropylethylamine; DMF is dimethylformamide; Fmoc is 9-fluorenylmethyl carbamate; HCTU is 2-(6-Chloro-1H-benzotriazole-1-yl)-1,1,3,3-tetramethylaminium hexafluorophosphate; NMM is N-methylmorpholine; TES is triethylsilane; TFA is trifluoroacetic acid; and THF tetrahydrofuran.

Compounds of formula (I) may be synthesized as shown in Schemes 1 and 2.

(N2-Boc)-α-hydrazino acids may be prepared from proteinogenic amino acids using a practical two-step protocol as shown in Scheme 1. In the majority of cases, commercially available and inexpensive α-amino ester hydrochloride salts (bearing acid-labile side chain protecting groups for Fmoc SPPS) can be used as substrates. The Cys, Trp, Asn, and Gln substrates, which are not readily available as hydrochloride salts, may be prepared from the corresponding Fmoc-protected derivatives and used in their neutralized amine form. Saponifications yield (N2-Boc)-α-hydrazino acids, which are soluble in EtOAc following acidification of the aqueous layer. In most cases, trituration of the crude carboxylic acids with hexanes results in pure products.

Scheme 1:

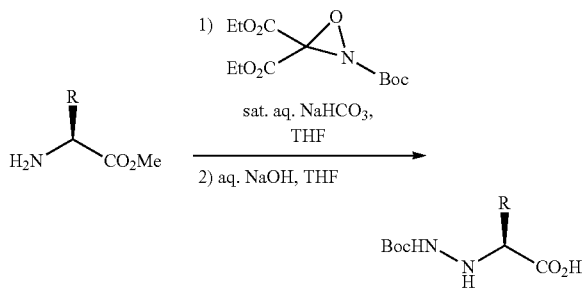

Any established solid-phase peptide synthesis method may be used to generate the compounds described herein. The N-aminated peptides of formula (I) may be assembled using standard 9-fluorenylmethyl carbamate (Fmoc) protection chemistry; employing successive Fmoc deprotections followed by couplings of Fmoc-protected amino acids or (N2-Boc)-α-hydrazino acids. The coupling agent may be chosen from any of the conventional coupling agents used in peptide synthesis including, for example, benzotriazol-1-yloxytris-(dimethylamino)-phosphonium hexaflurophosphate (BOP), dicyclohexylcarbodiimide (DCC), 1-hydroxybenzotriazole (HOBT), diisopropylethylamine (DI EA), O-(benxotriazol-1-yl)-1,1,3,3-tetramethyluronium hexafluorophosphate (HBTU), 2-(6-Chloro-1H-benzotriazole-1-yl)-1,1,3,3-tetramethylaminium hexafluorophosphate (HCTU) and O-(7-Azabenzotriazol-1-yl)-N, N, N',N'-tetramethyluronium hexafluorophosphate (HATU). Separation of the peptide from the solid supports can be done in a single step by treatment with an acid. When the separation is carried out with trifluoroacetic acid, the amino group may be protected with an Fmoc group. The hydrazino acid building blocks may be used in the synthesis of N-aminated peptides on Rink amide MBHA resin as shown in Scheme 2.

Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and T W Greene, in Greene's book titled Protective Groups in Organic Synthesis (4th ed.), John Wiley & Sons, NY (2006), which is incorporated herein by reference in its entirety. Synthesis of the compounds of the disclosure can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induc- Scheme 2:

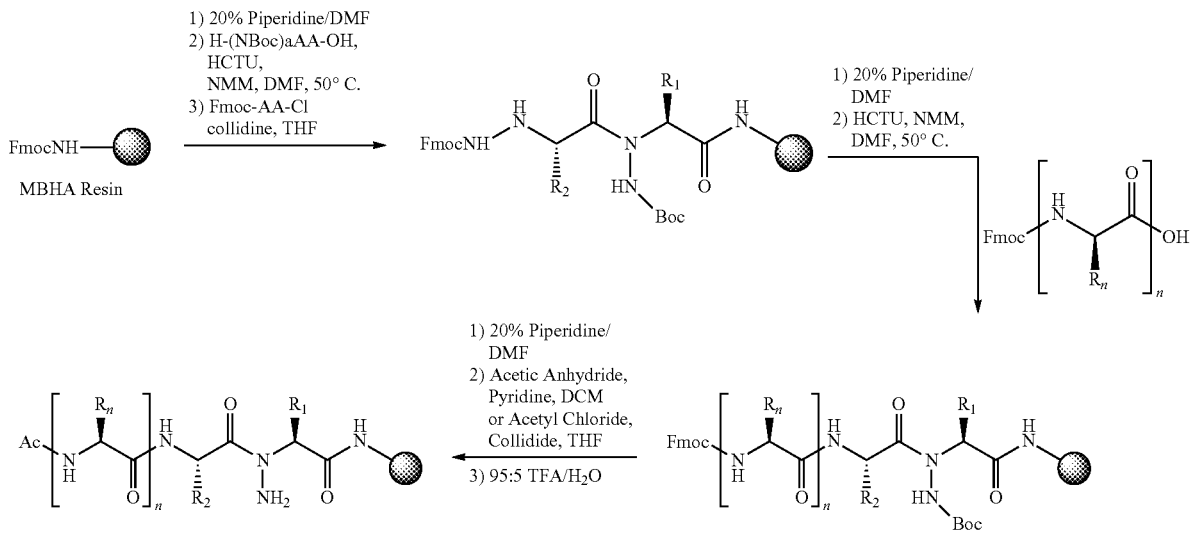

Reaction conditions and reaction times for each individual step can vary depending on the particular reactants employed and substituents present in the reactants used. Specific procedures are provided in the Examples section.

tion of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the disclosure as it is defined in the appended claims. All alternatives, modifications, and equivalents of the synthetic methods and specific examples are included within the scope of the claims.

3. PHARMACEUTICAL COMPOSITIONS

The disclosed compounds may be incorporated into pharmaceutical compositions suitable for administration to a subject. The pharmaceutical composition may comprise the compound and a pharmaceutically acceptable carrier.

The pharmaceutical compositions may include a therapeutically effective amount of the compound. Any suitable therapeutically effective amount of the compound may be used in the pharmaceutical composition. For example, a therapeutically effective amount may be about 0.001 mg/kg to about 1000 g/kg, 0.01 mg/kg to about 100 g/kg, 0.1 mg/kg to about 10 g/kg, 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical composition may further comprise one or more pharmaceutically acceptable carriers. Pharmaceutically acceptable carriers typically include at least one of diluents, lubricants, binders, disintegrants, colorants, flavors, sweeteners, antioxidants, preservatives, glidants, solvents, suspending agents, wetting agents, surfactants, pH adjusting additives, combinations thereof, and others. The route by which the disclosed compounds are administered and the form of the composition will dictate the type of carrier to be used.

The pharmaceutical composition may be in a variety of forms, suitable for any desired mode of administration. For example, the composition may be in a form that is suitable for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis).

The term parenteral as used herein includes subcutaneous, intravenous, intramuscular, intrathecal, or intrasternal injection, or infusion techniques. Injectable preparations, for example, sterile injectable aqueous or oleaginous suspensions, may be formulated according to the known art using suitable pharmaceutically acceptable carriers. The sterile injectable preparation may also be a sterile injectable solution or suspension in a nontoxic pharmaceutically acceptable carrier. Among the acceptable carriers that may be employed are water, Ringer's solution, isotonic sodium chloride solution. In addition, sterile, fixed oils may be used as a carrier. For this purpose, any bland fixed oil may be employed, including synthetic mono- or diglycerides. In addition, fatty acids such as oleic acid may be used. Other suitable pharmaceutically acceptable carriers include dimethyl acetamide, surfactants including ionic and non-ionic detergents, and polyethylene glycols. The disclosed compositions may be sterile and stable under the conditions of manufacture and storage. For this purpose, suitable preservatives may be used in the disclosed compositions. For example, the disclosed compositions may comprise benzalkonium chloride, methyl paraben and/or sodium benzoate. The amount of preservative(s) in a composition is typically about 0.01 to about 5%. Suitable pH adjusting additives may also be added to the pharmaceutical composition. Suitable pH adjusting additives include HCl or NaOH in amounts sufficient to adjust the pH of the pharmaceutical composition. Mixtures of pharmaceutically acceptable carriers such as those discussed above may also be used.

4. METHODS OF USE

The disclosure provides a method for reducing or inhibiting amyloid-beta aggregation in a subject. The method may comprise administering an effective amount of the disclosed compounds or compositions to a subject. For example, the disclosed compounds or compositions may reduce or inhibit amyloid-beta fibrillation. Amyloid-beta aggregation or fibrillation may be reduced or inhibited relative to a control. In some embodiments, amyloid-beta aggregation or fibrillation is reduced or inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, or at least about 99% relative to a control. In some embodiments, the control is a healthy subject or sample therefrom, a subject or sample therefrom without or prior to treatment, or a subject or sample therefrom at any point earlier in treatment.

The disclosure further provides a method for treating Alzheimer's disease in a subject. The method may comprise administering a therapeutically effective amount of the disclosed compounds or compositions to the subject. The subject may be diagnosed with or at risk of developing Alzheimer's disease. The subject may be undergoing other forms of treatment for Alzheimer's disease. In Alzheimer's disease patients, two distinct types of fibrillar protein aggregates are commonly found in brain samples: amyloid plaques comprising deposits of amyloid-beta protein (Aβ) and neurofibrillary tangles consisting of the microtubule-associated protein tau. Genetic and neuropathologic studies suggest that the accumulation of amyloid plaques and/or neurofibrillary tangles may be central to the pathogenesis of Alzheimer's disease.

The disclosed compounds or compositions may be administered to the subject by any suitable route. For example, the disclosed compounds or compositions may be administered orally, parentally, by infusion, by electroporation, or co-administered as a component of any medical device or object to be inserted (temporarily or permanently) into a subject.

Administration methods are preferably those that are effective to circumvent the blood-brain barrier and are effective to deliver the disclosed compounds or compositions to the central nervous system. For example, delivery methods may include the use of nanoparticles. The particles may be of any suitable structure. Positively charged lipids are particularly preferred for the formulation of such nanoparticles. The preparation of such lipid particles is well known in the art. See, e.g., U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

The disclosed compounds or compositions may be administered in a bolus directly into the central nervous system. The composition may be administered to the subject in a bolus once, or multiple times. When administered multiple times, the compositions may be administered at regular intervals or at intervals that may vary during the treatment of a subject.

The disclosed compounds or compositions may be administered by continuous infusion into the central nervous system. Non-limiting examples of methods that may be used to deliver the disclosed compounds or compositions into the central nervous system by continuous infusion may include pumps, wafers, gels, foams and fibrin clots. For example, the disclosed compounds or compositions may be delivered into the central nervous system by continuous infusion using an osmotic pump.

The disclosed compounds or compositions may be administered to the patient at any frequency necessary to achieve the desired therapeutic effect. The disclosed compounds or compositions may be administered to the subject as a single dose, or multiple doses over a period of time. For example, the compounds or compositions may be administered once to several times every month, every two weeks, every week, or every day. Administration of the compounds or compositions may be repeated until the desired therapeutic effect has been achieved. For example, the compounds or compositions may be administered once to several times over the course of 1 day, 3 days, 5 days, 1 week, 2 weeks, 3 weeks, 1 month, 2 months, 3 months, 4 months, 5 months, 6 months, 7 months, 8 months, 9 months, 10 months, 11 months, 12 months, or more.

The amount of the compounds or compositions to be administered may depend on a variety of factors, such as the route of administration and the seriousness of the condition, and should be decided according to the judgment of the practitioner and each patient's circumstances. The compounds or compositions may be administered in any amount suitable to achieve the desired therapeutic effect. Suitable dosage ranges of the disclosed compounds or compositions include from about 0.001 mg compound/kg body weight to about 1000 g/kg, 0.01 mg/kg to about 100 g/kg, 0.1 mg/kg to about 10 g/kg, 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The disclosed compounds or compositions may be administered to the subject in combination with other therapies. For example, the disclosed compounds or compositions may be administered to the subject with other therapies to reduce aggregation of amyloid-beta. As another example, the disclosed compounds or compositions may be administered to the subject in combination with other therapies for the treatment of Alzheimer's disease.

5. EXAMPLES

The disclosed compounds, compositions, processes, and methods will be better understood by reference to the following examples, which are intended as an illustration of and not a limitation upon the scope of the invention. Where the term comprising is used herein, it should be understood that the disclosure also contemplates alternative embodiments consisting of or consisting essentially of the recited features.

Example 1

Exemplary Synthesis of (N2-Boc)-α-hydrazino Acids

The α-amino acid methyl ester or α-amino acid methyl ester hydrochloride salt (0.173 mmol) was suspended in a mixture of 2.5 mL of THF and 2.5 mL of saturated aqueous NaHCO$_3$, and the mixture was vigorously stirred for 10 minutes at room temperature. After addition of an N-Boc-oxaziridine derivative, 2-(tert-butyl) 3,3-diethyl 1,2 oxaziridine-2,3,3-tricarboxylate (50.0 mg, 0.173 mmol), the reaction was stirred for 2 hours at room temperature. The reaction was then treated with 50 µL of ethylenediamine. The mixture was absorbed onto 3 g of silica gel and concentrated in vacuo to dryness. The crude materials were purified by silica gel flash chromatography (EtOAc/hexanes) to give (N2-Boc)-α-hydrazino esters.

The (N2-Boc)-α-hydrazino esters were dissolved in 1.5 mL of THF and 1.5 mL of 1.0 M aqueous NaOH, and the mixtures were stirred for 1-4 hours at room temperature. The reaction mixture was diluted with water (10 mL) and washed with Et2O, and the aqueous layer was acidified to pH 1 with 1 M aqueous HCl. The aqueous solution was extracted with EtOAc, the organic layer was dried over anhydrous MgSO$_4$, and the solvent was removed in vacuo to give the corresponding N-hydrazo amino acid. In some cases, 2 equivalents of LiOH was used for hydrolysis in place of 1 M aqueous NaOH. The crude materials were purified by either silica gel flash chromatography (MeOH/DCM) or trituration with hexanes to give the (N2-Boc)-α-hydrazino acids. Detailed syntheses for the (N2-Boc)-α-hydrazino acids corresponding to each amino acid can be found in Kang et. al. *J. Org Chem.* 2017, 82, 1833-1841), which is incorporated herein by reference in its entirety.

Example 2

Exemplary Solid-Phase Peptide Synthesis Using Fmoc-Protected Amino Acids and (N2-Boc)-α-Hydrazino Acids Solid-phase peptide synthesis was carried out on Fmoc-capped polystyrene rink amide MBHA resin (100-200 mesh). Dry resin was washed with DMF three times and allowed to swell in DMF for 2 hours prior to use. All reactions were carried out using gentle agitation. Fmoc deprotection steps were carried out by treating the resin twice with a solution of 20% piperidine/DMF (15 min). Coupling of Fmoc-protected amino acids as well as (N2-

Boc)-α-hydrazino acids was effected using 5 equivalents of HATU (0.5 M in DMF), 10 equivalents of DIEA (1.0 M in DMF), and 5 equivalents of the carboxylic acid in DMF at 50° C. (1 hour). Coupling of residues N-terminal to the hydrazino acids was carried out with 30 equivalents of collidine and 10 equivalents of preformed Fmoc amino acid chloride in THF at 45° C. (twice for 1 hour). After each reaction, the resin was washed with DMF three times.

Peptides were cleaved from the resin by incubating with gentle stirring in 95:5 TFA/H2O or 45:45:10 TFA/DCM/TES at room temperature for 4 hours. The cleavage mixture was filtered, and the resin was rinsed with additional cleavage solution. The filtrate was concentrated to remove the bulk of the TFA, and the remaining residue was treated with 8 mL of cold diethyl ether to induce precipitation. The mixture was centrifuged, and the supernatant was removed. The remaining solid was washed two more times with diethyl ether and dried under vacuum. Peptides were analyzed and purified on C12 RP-HPLC columns (preparative: 4 μm, 90 Å, 250×21.2 mm; analytical: 4 μm, 90 Å, 150×4.6 mm) using linear gradients of MeCN/H$_2$O (with 0.1% formic acid) and then lyophilized to afford white powders. All peptides were characterized by LCMS (ESI), HRMS (ESI-TOF), and 1H NMR.

Example 3

Inhibition of Aβ42 Fibrillation with N-Aminated Peptides

Figure 2A:
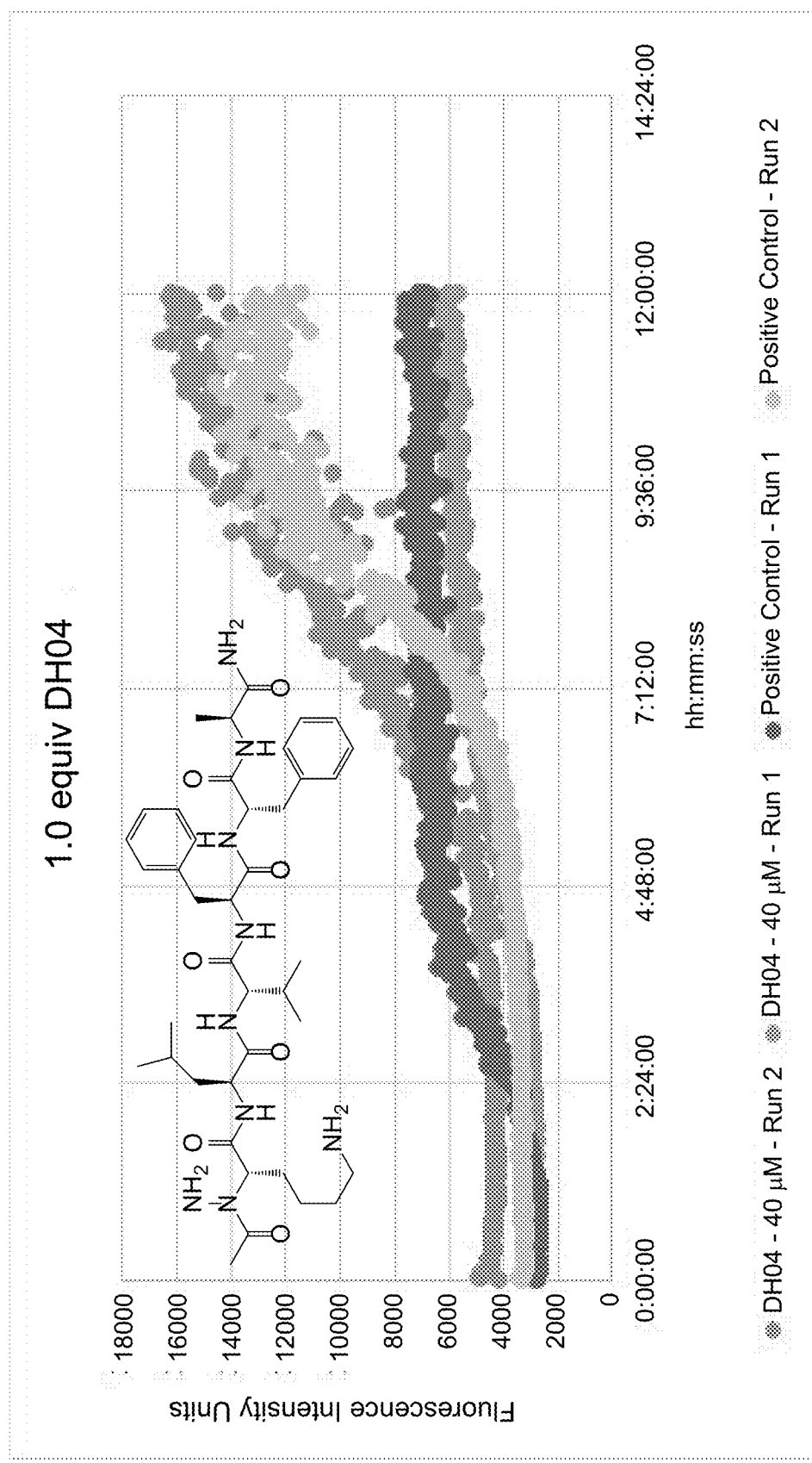
FIGS. 2A-2O show results from a thioflavin T (ThT) assay for anti-fibrillization activity against Aβ42 with representative peptides: DH04 (FIG. 2A), DH05 (FIG. 2B), DH06 (FIG. 2C), DH07 (FIG. 2D), DH08 (FIG. 2E), DH09 (FIG. 2F), EA01 (FIG. 2G), EA02 (FIG. 2H), EA03 (FIG. 2I), EA04 (FIG. 2J), EA05 (FIG. 2K), EA06 (FIG. 2L), EA07 (FIG. 2M), EE01 (FIG. 2N), and EA09 (FIG. 2O). 40 μM Aβ42 was incubated with 40 μM ThT and various concentrations (20 μM, 40 μM, or 80 μM) of potential inhibitory N-aminated peptides. ThT fluorescence was monitored every minute at 484 nm.
Figure 2B:
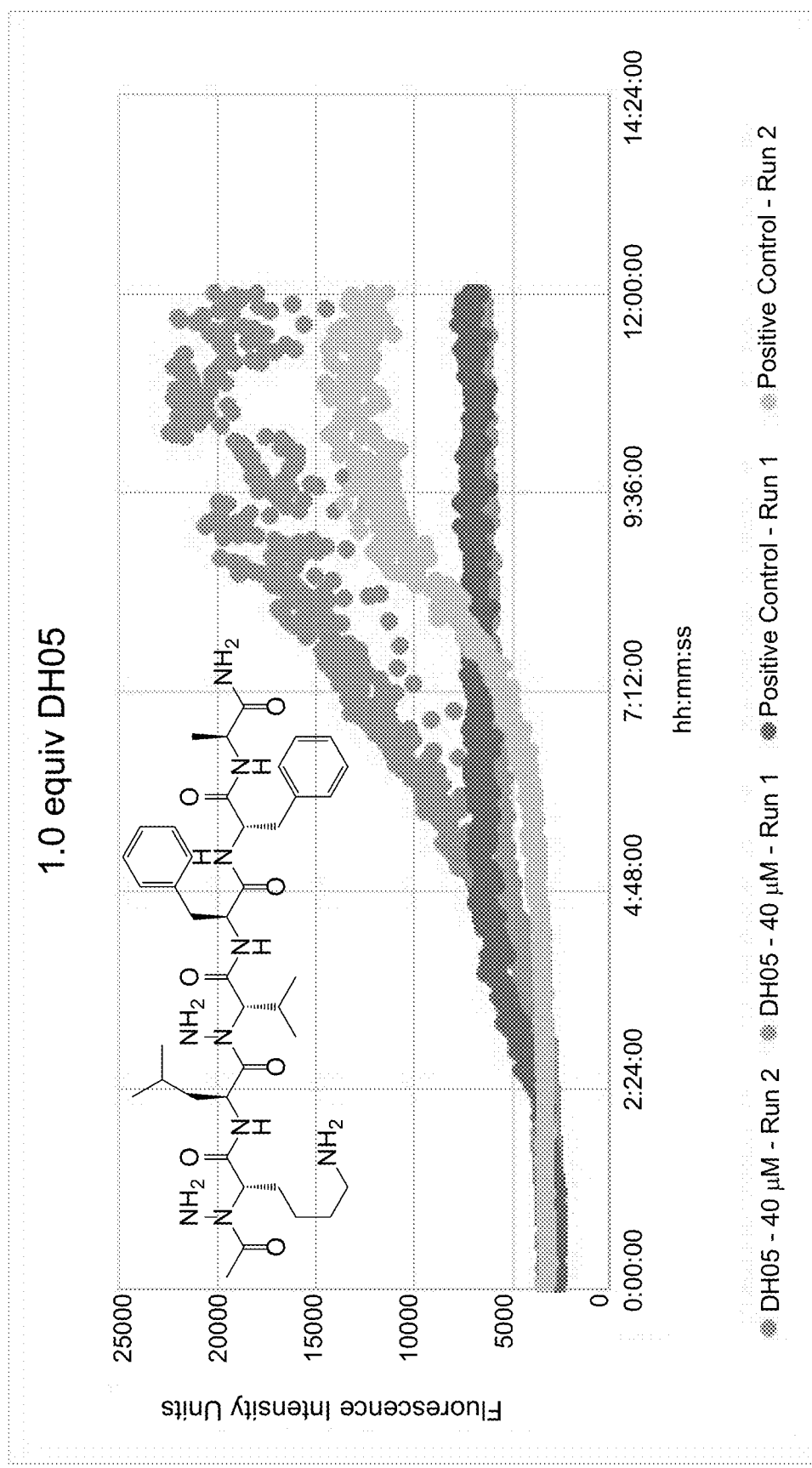
Figure 2C:
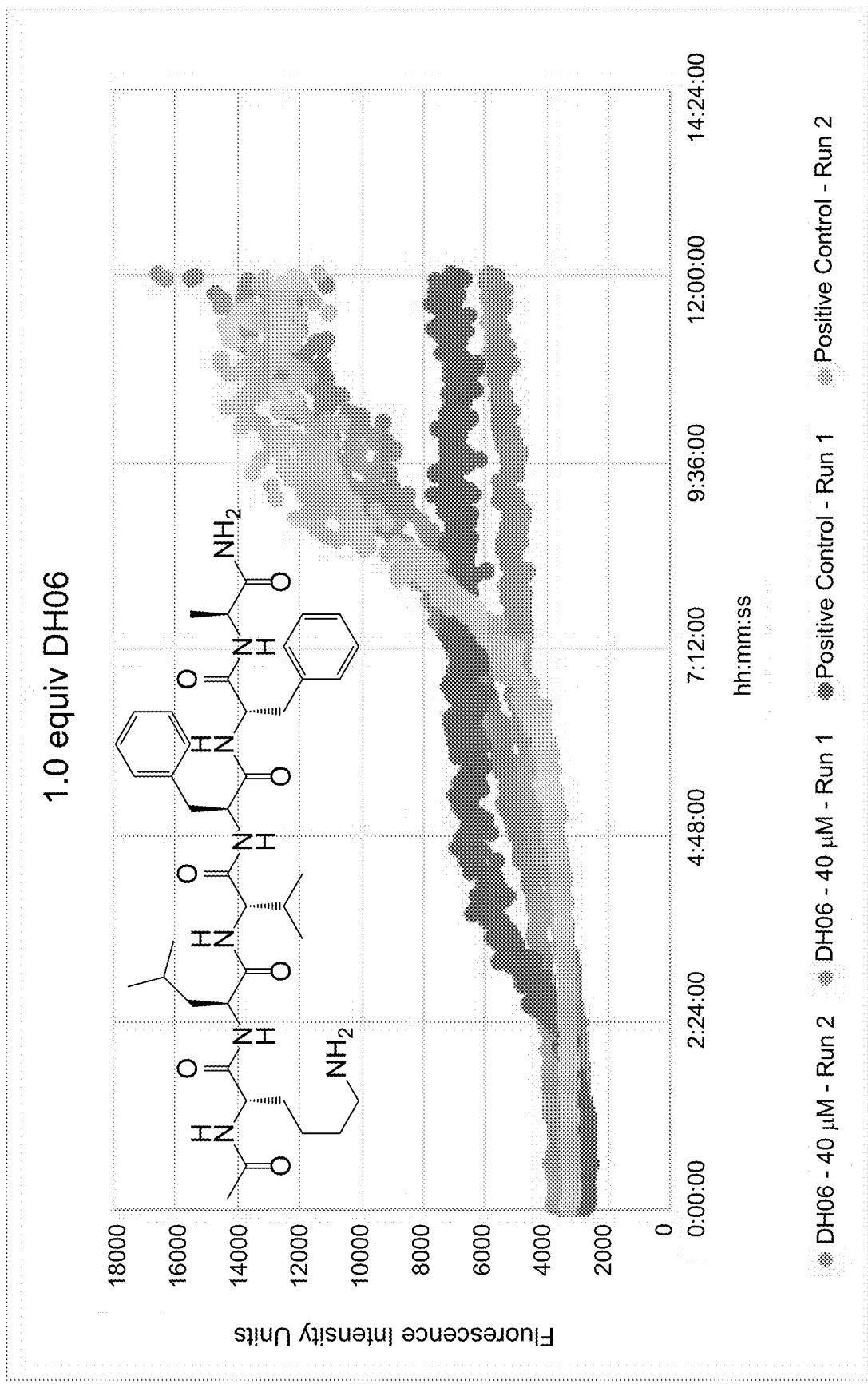
Figure 2D:
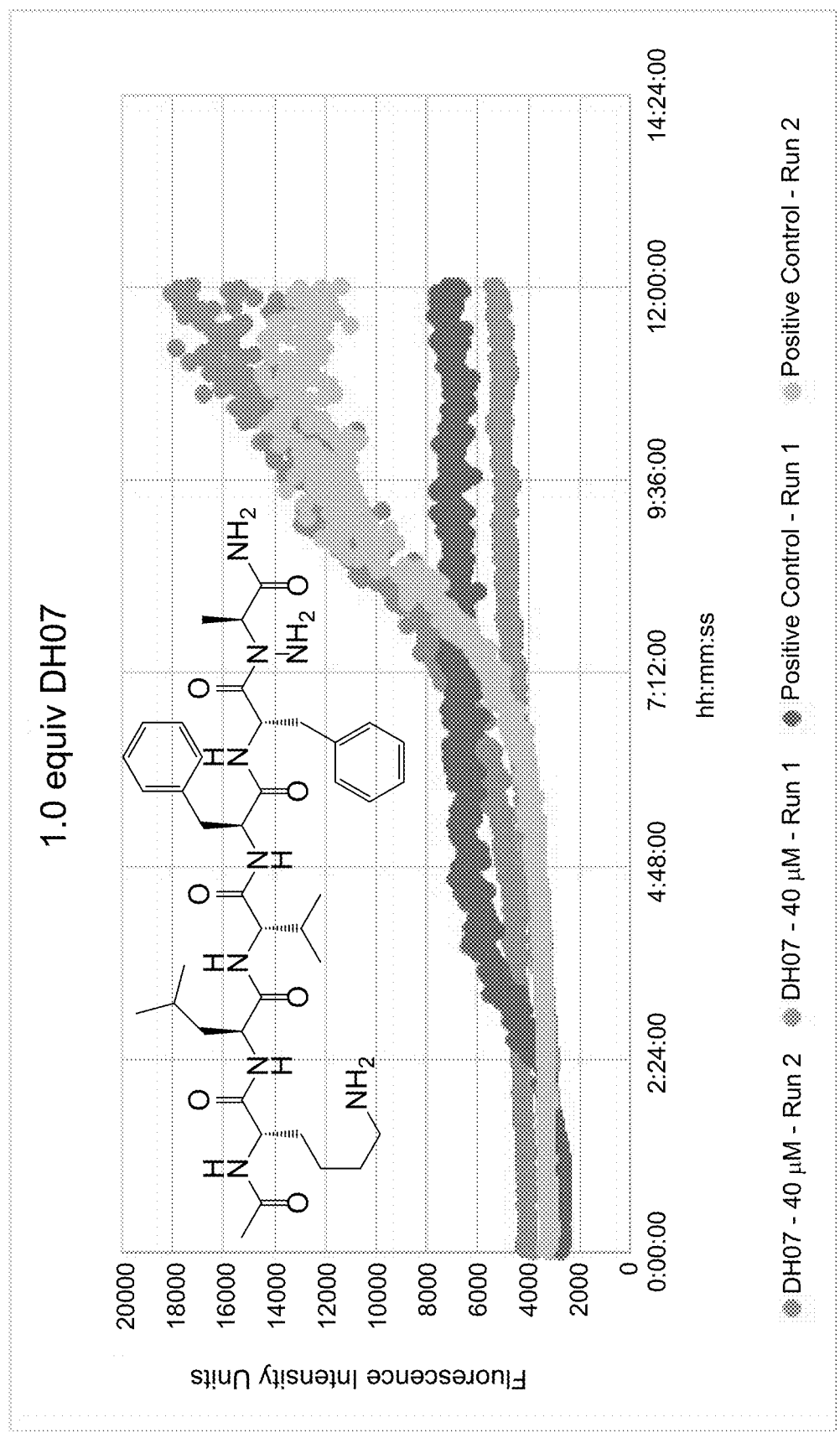
Figure 2E:
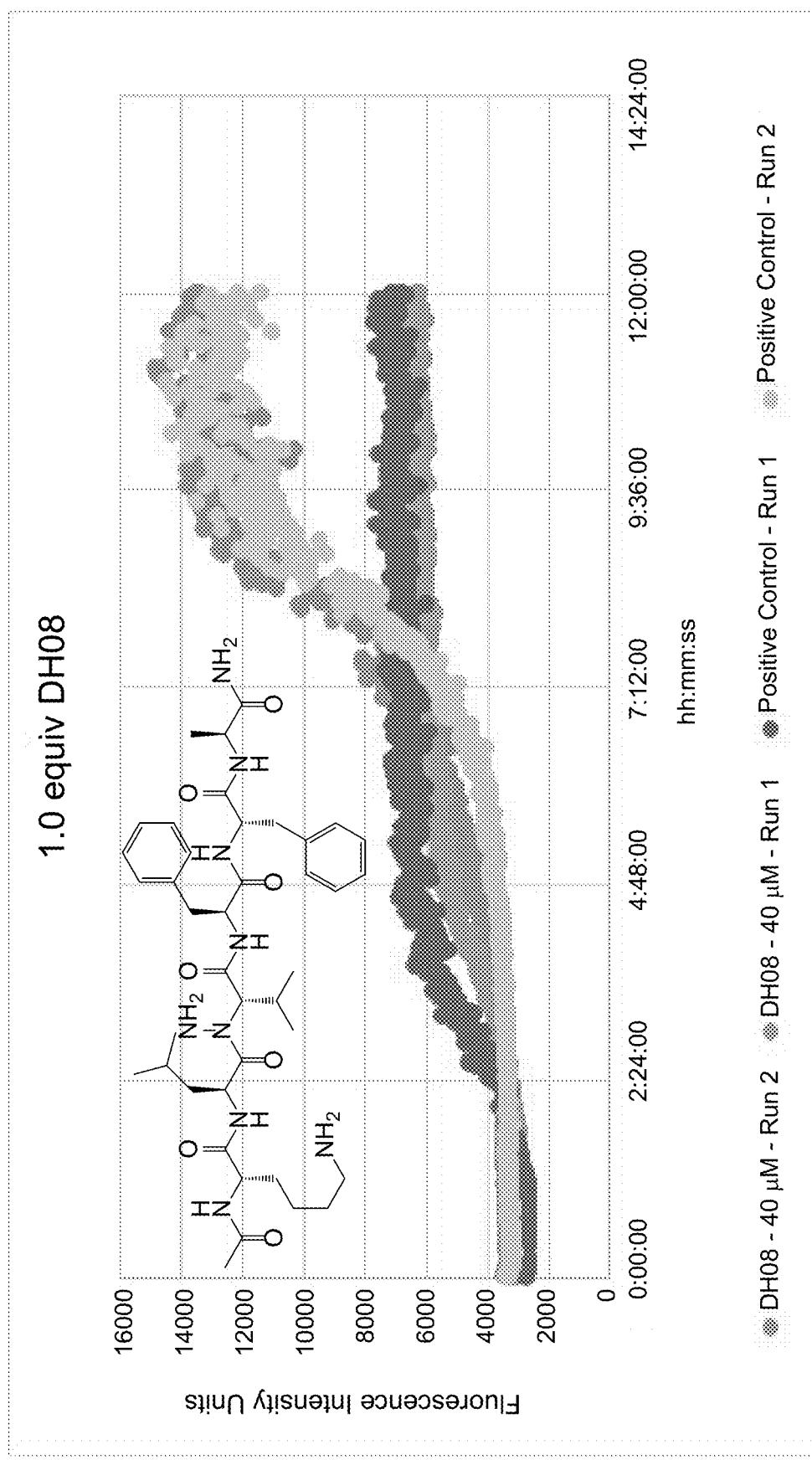
Figure 2F:
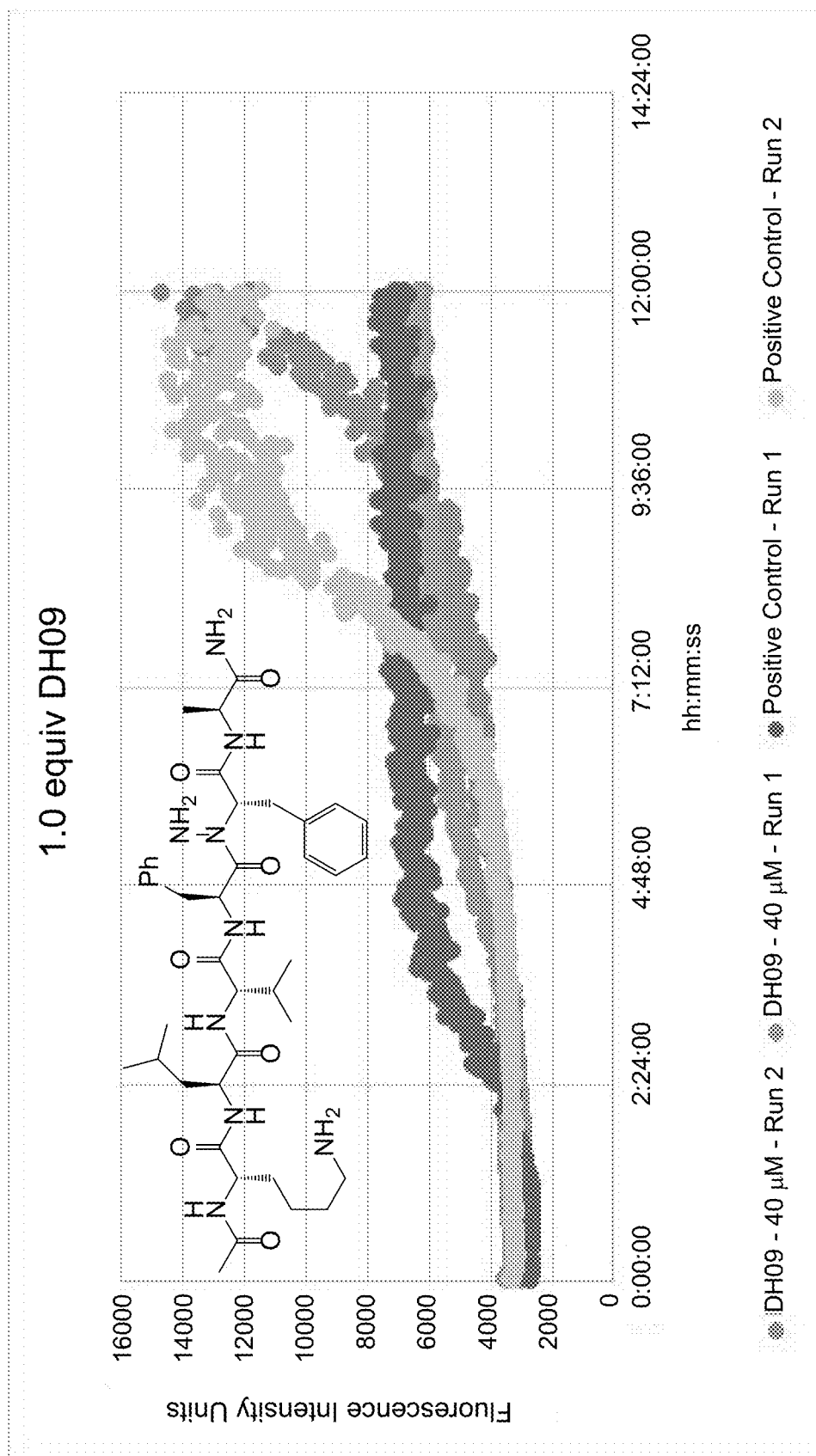
Figure 2G:
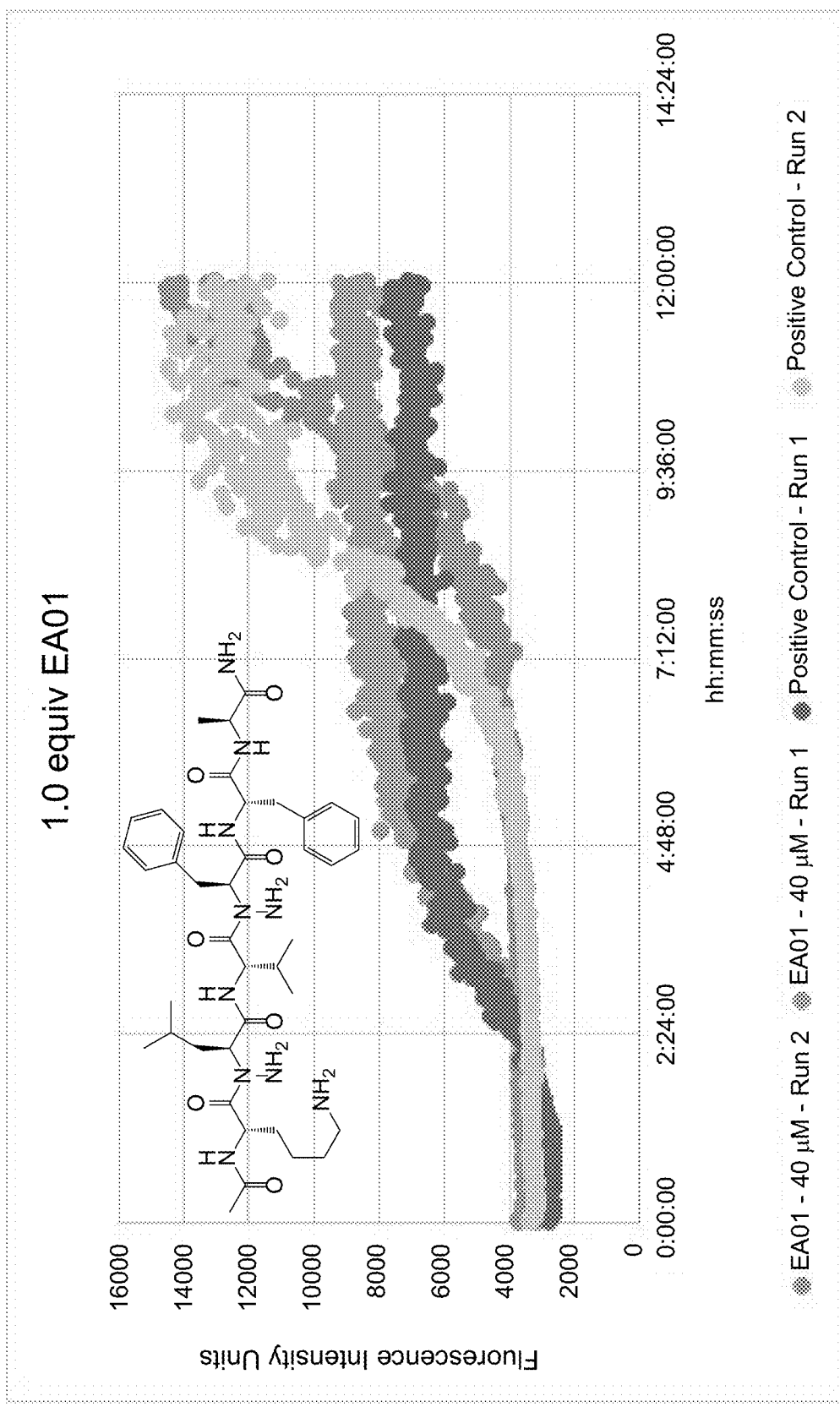
Figure 2H:
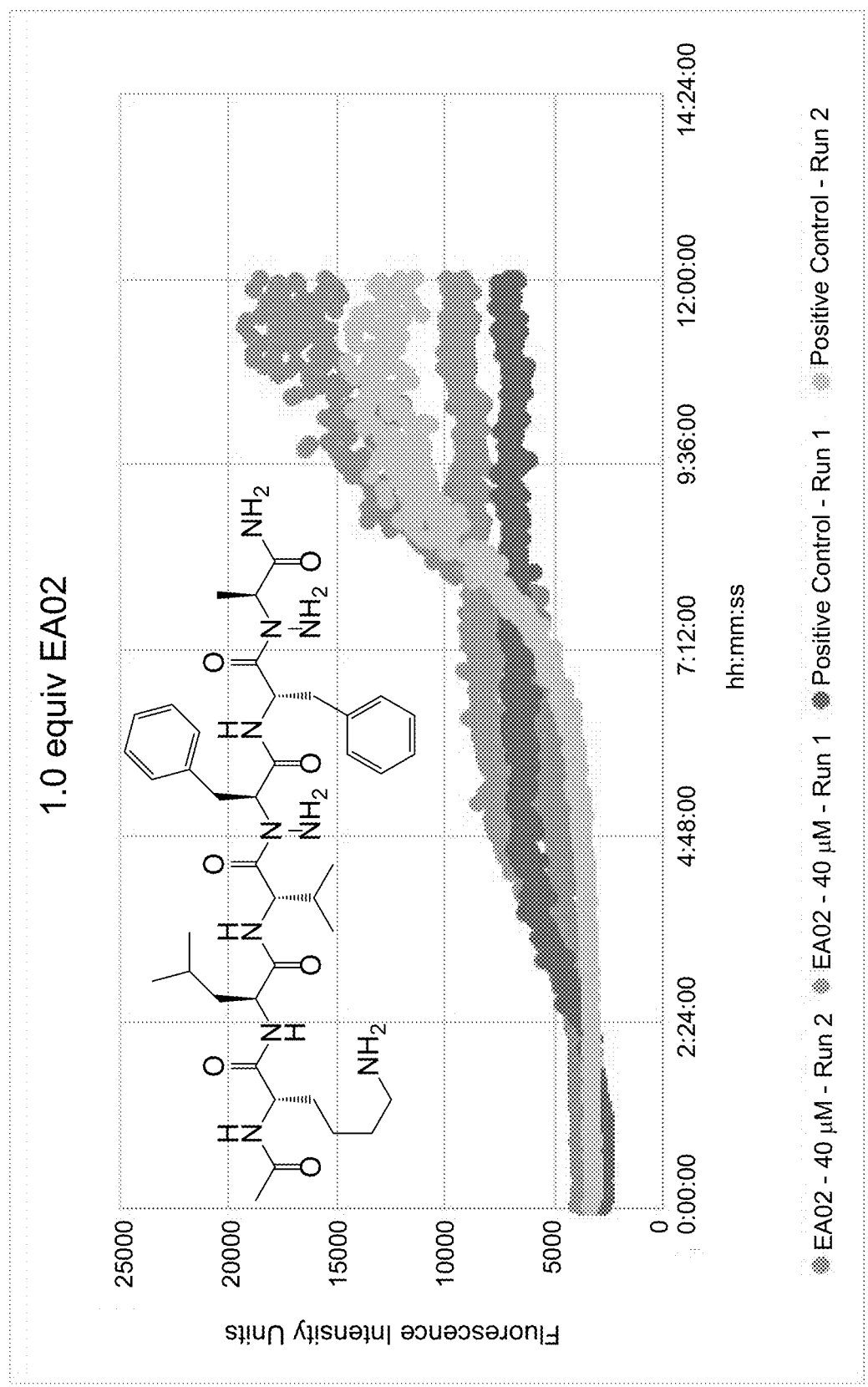
Figure 2I:
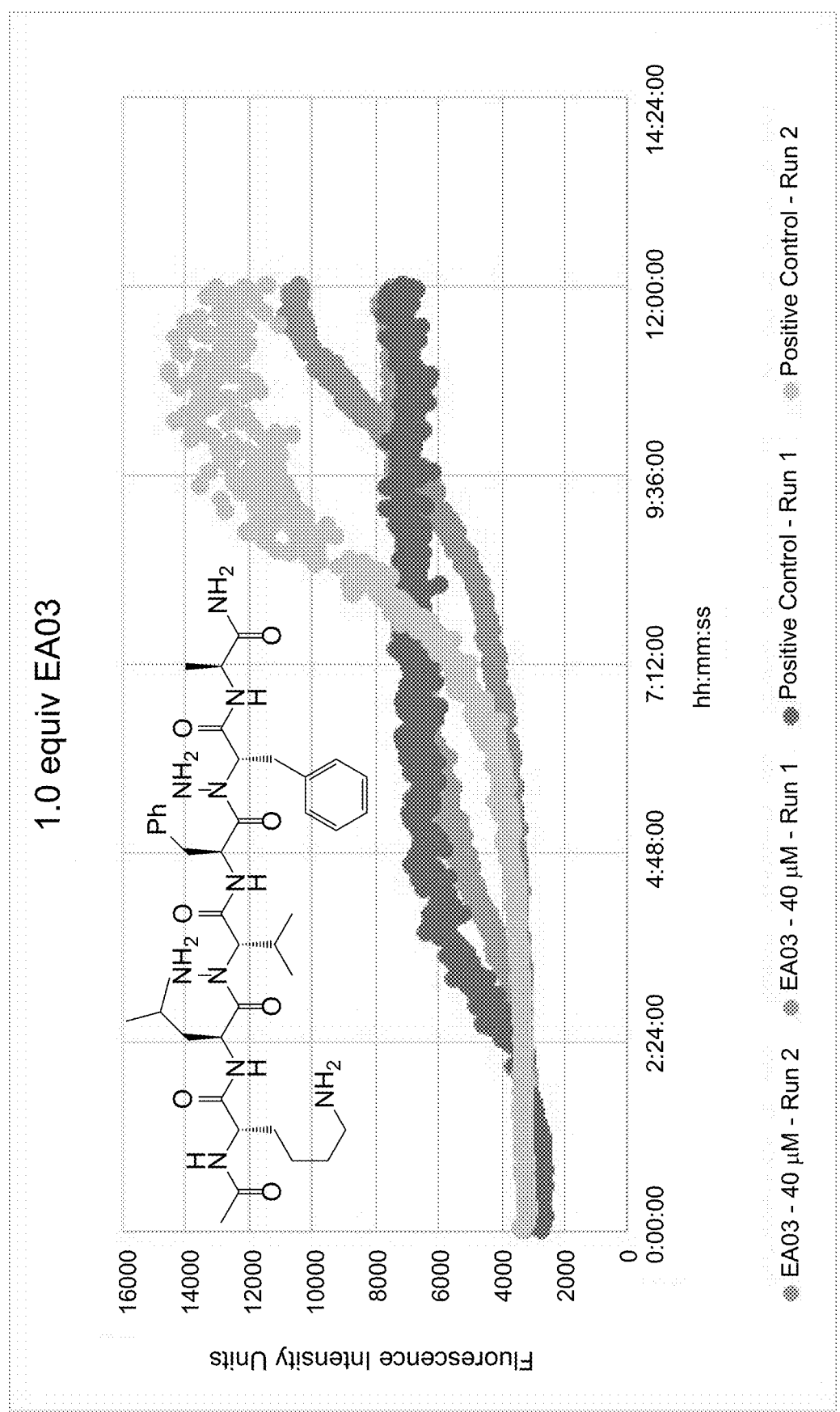
Figure 2J:
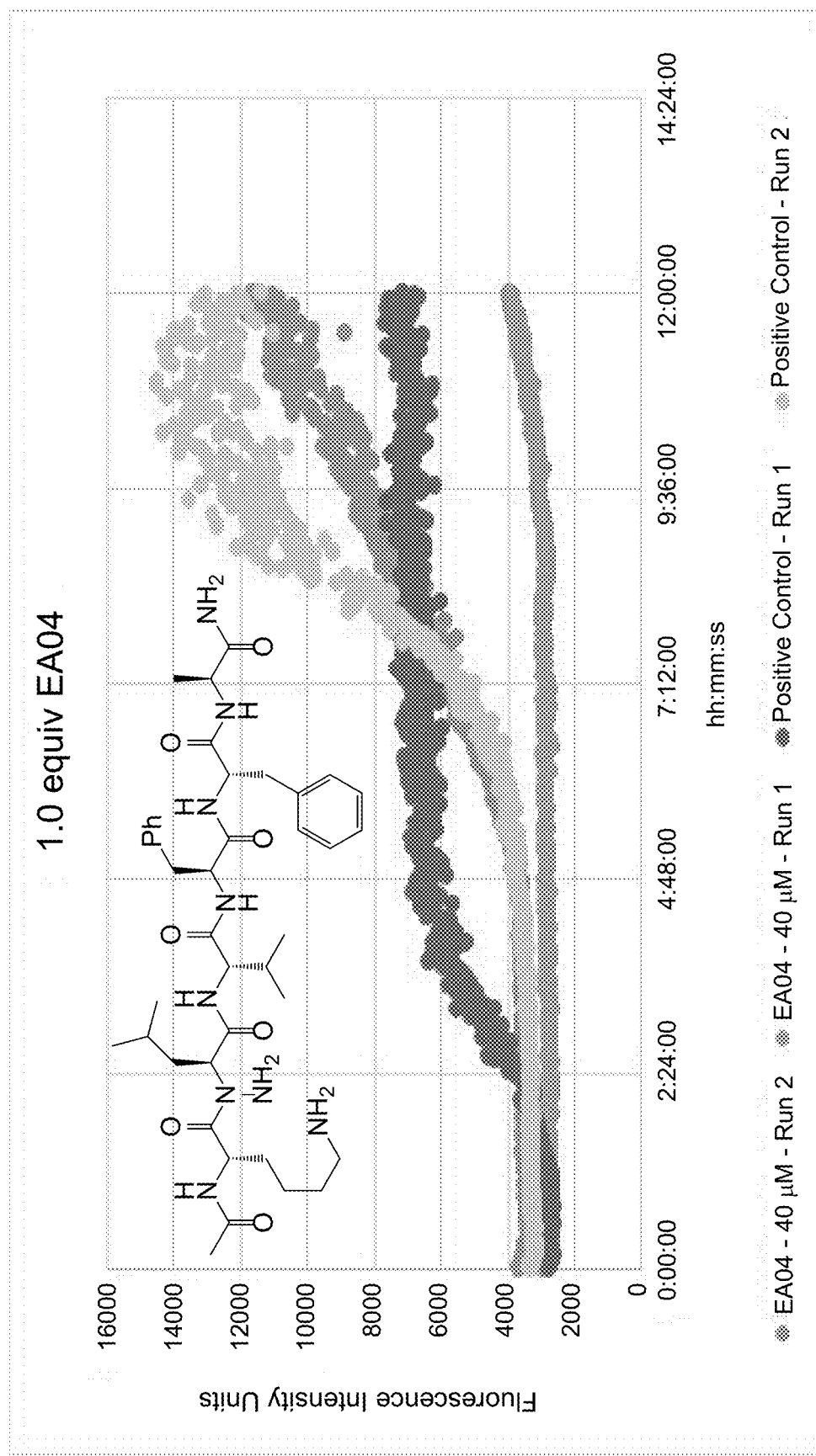
Figure 2K:
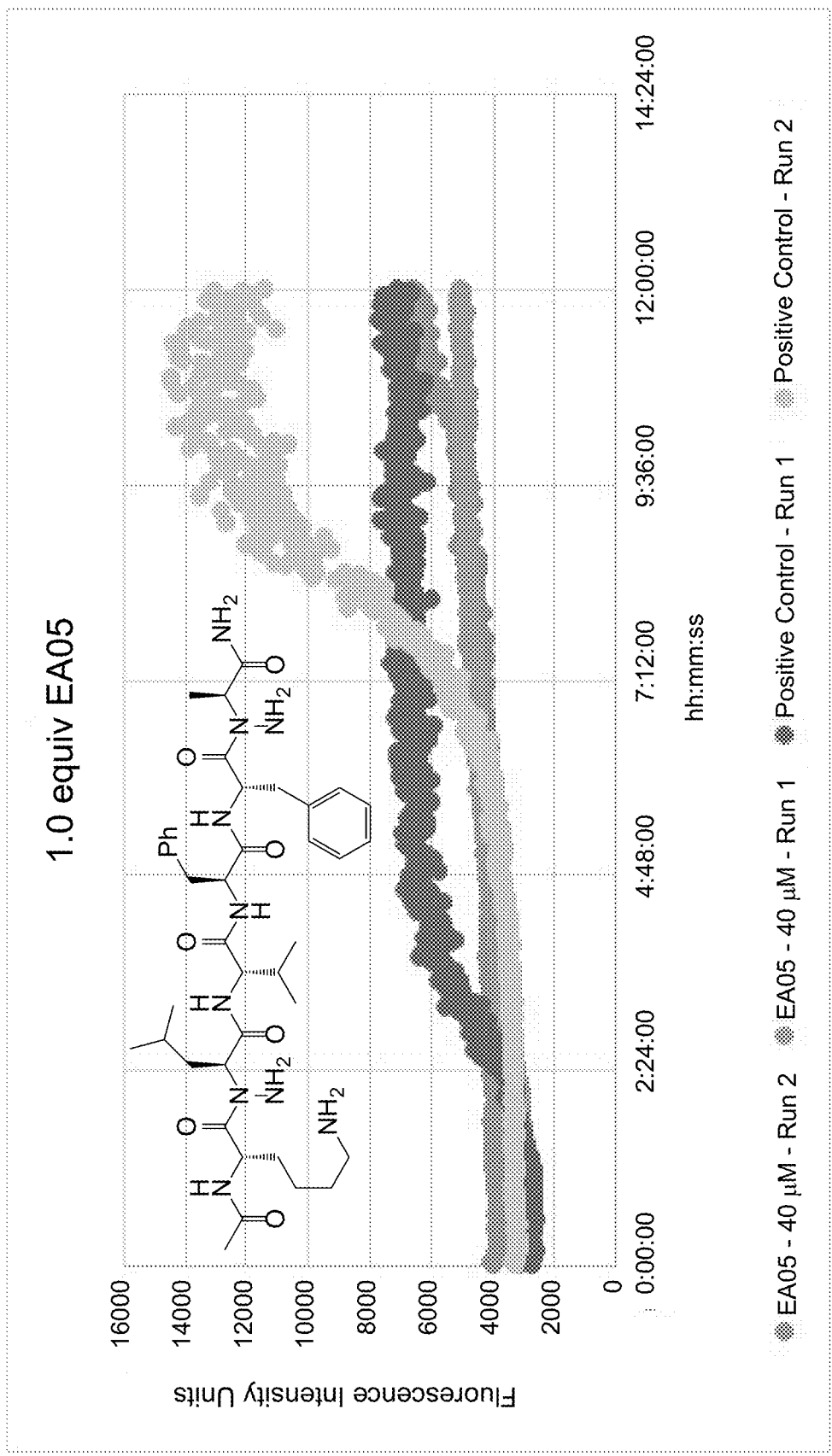
Figure 2L:
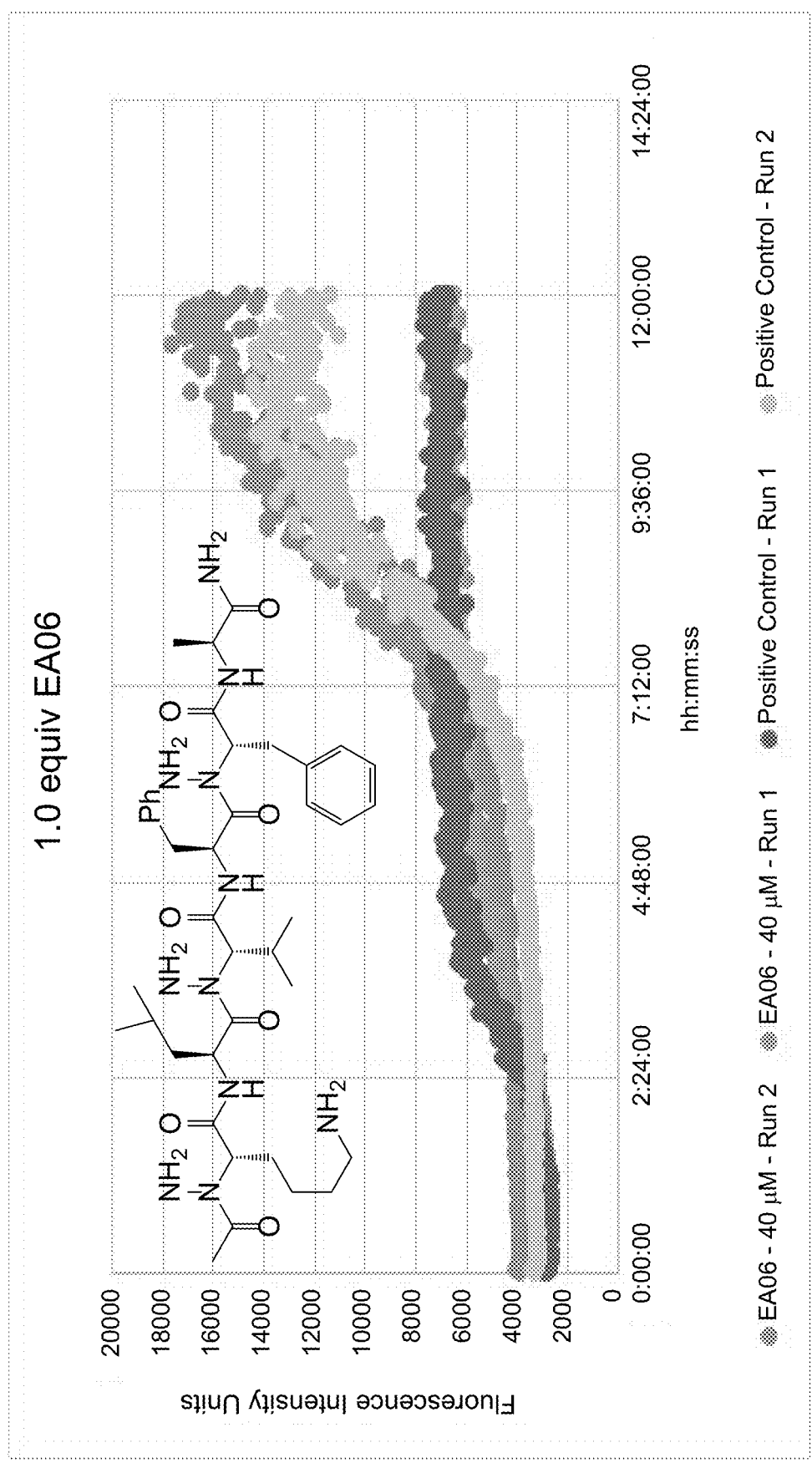
Figure 2M:
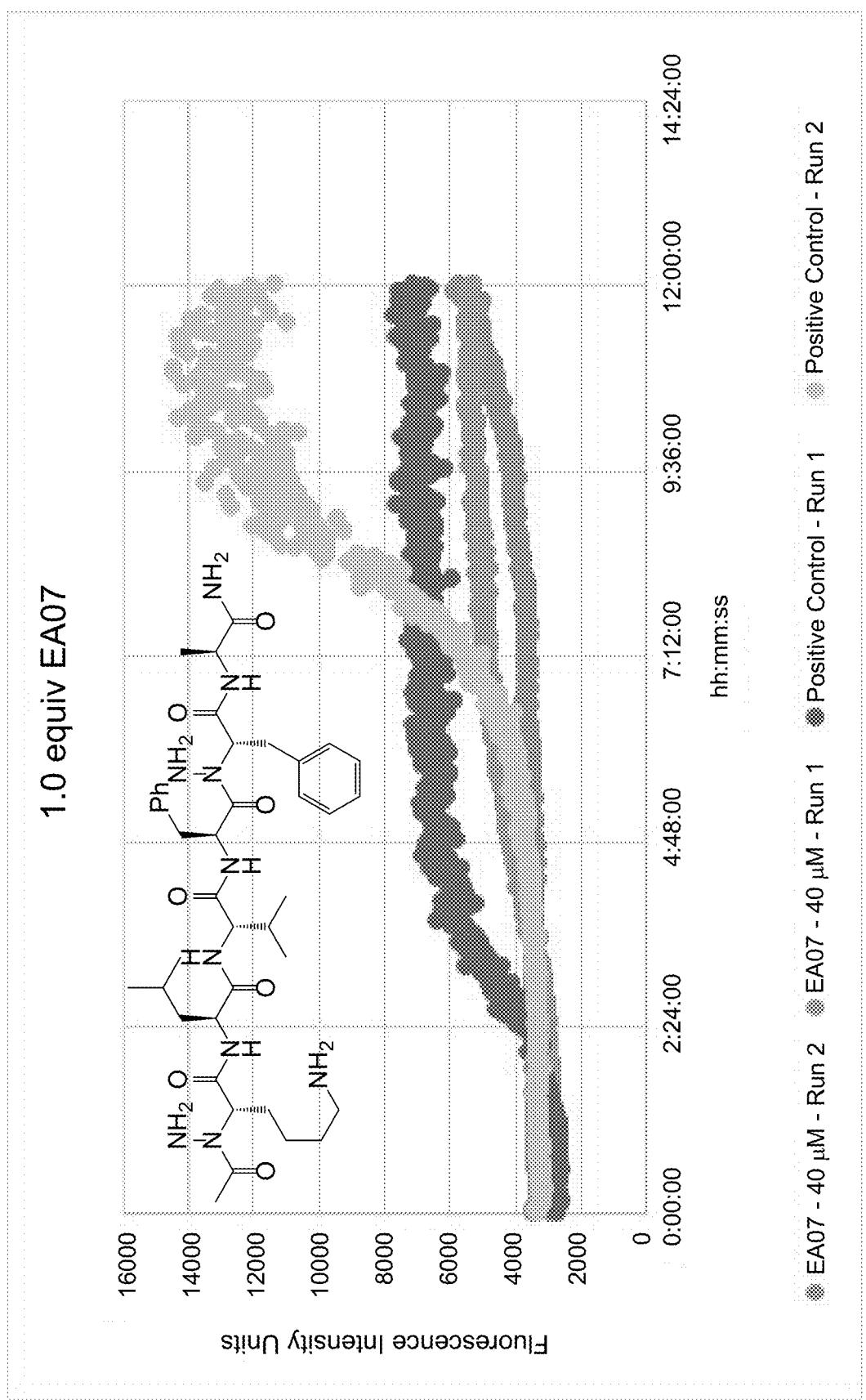
Figure 2N:
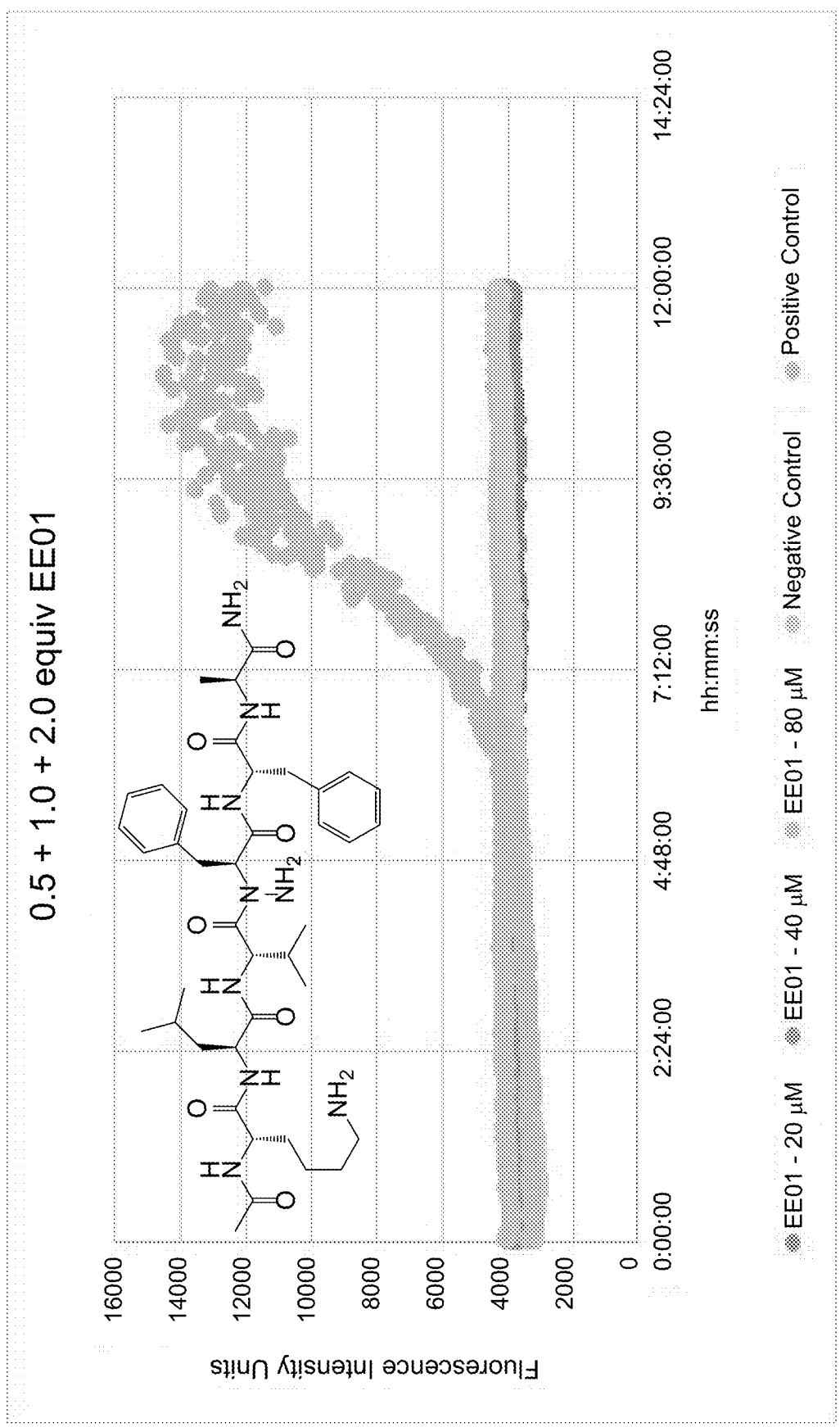
Figure 2O:
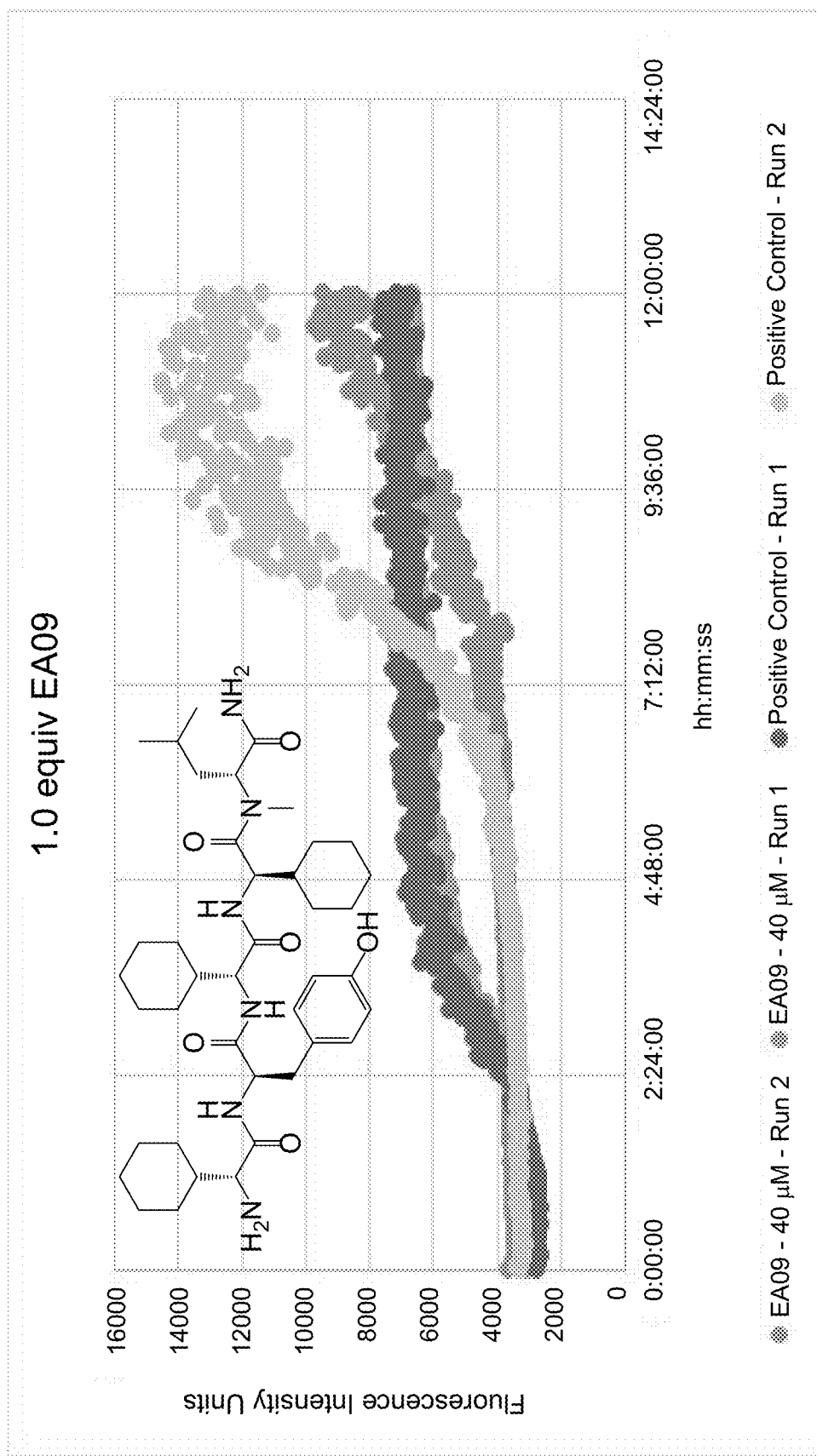

To assess the ability of the compounds described herein to inhibit amyloid-beta fibril formation, fibrillation assays were used. The degree of amyloid-beta fibril formation was assessed using Thioflavin T (ThT) as molecular indicator. 40 μM Aβ42 was incubated with 40 μM ThT and various concentrations (20 μM, 40 μM, or 80 μM) of potential inhibitory N-aminated peptides. 1 mg of purified Aβ42 TFA salt was treated with HFIP (hexafluoroisopropanol) and evaporated to dryness with high vacuum. The residue was dissolved in 10 mM aqueous NaOH, sonicated for 30 seconds, and diluted with PBS buffer to form a stock solution of Aβ42 of 66.67 μM. The stock solution was filtered through pre-washed Centricon 100 kD MWCO filters at 6000×g for 15 minutes. The Aβ42 stock solution was prepared as needed to minimize premature fibril formation. Each N-aminated peptide inhibitor was dissolved in 10% DMSO/PBS. ThT was dissolved in PBS and the exact concentration was determined by UV absorbance. Positive controls contained no peptide inhibitors. The reactions were incubated at 37° C. without shaking. ThT fluorescence was monitored every minute at 484 nm; 440 nm excitation. Results are shown in FIG. 2A-FIG. 2O.

For reasons of completeness, various aspects of the invention are set out in the following numbered clauses:

Clause 1: A compound of formula (I),

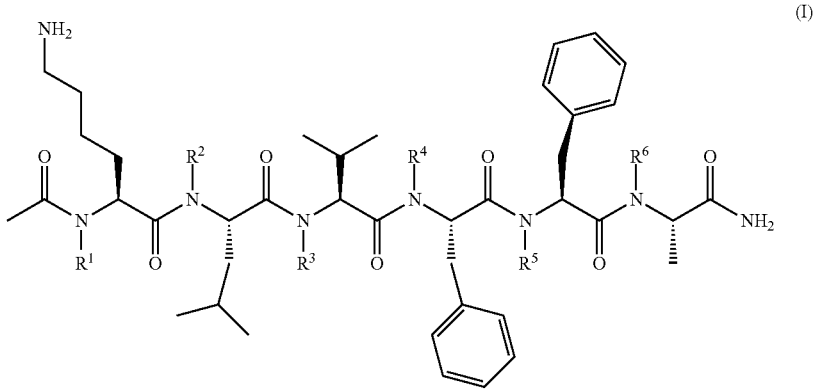

or a pharmaceutically acceptable salt thereof, wherein $R^1$, $R^2$, $R^3$, $R^4$, $R^5$, and $R^6$ are each independently selected from hydrogen or —NH$_2$.

Clause 2: The compound of clause 1, wherein at least one of $R^1$, $R^2$, $R^3$, $R^4$, $R^5$, and $R^6$ is —NH$_2$.

Clause 3: The compound of clause 1, wherein two of $R^1$, $R^2$, $R^3$, $R^4$, $R^5$, and $R^6$ are —NH$_2$.

Clause 4: The compound of clause 3, wherein W and $R^3$ are —NH$_2$.

Clause 5: The compound of clause 3, wherein W and $R^5$ are —NH$_2$.

Clause 6: The compound of clause 3, wherein $R^2$ and $R^4$ are —NH$_2$.

Clause 7: The compound of clause 3, wherein $R^2$ and $R^6$ are —NH$_2$.

Clause 8: The compound of clause 3, wherein $R^3$ and $R^5$ are —NH$_2$.

Clause 9: The compound of clause 3, wherein $R^4$ and $R^6$ are —NH$_2$.

Clause 10: The compound of clause 1, wherein three of $R^1$, $R^2$, $R^3$, $R^4$, $R^5$, and $R^6$ are —NH$_2$.

Clause 11: The compound of clause 10, wherein $R^1$, $R^3$ and $R^5$ are —NH$_2$.

Clause 12: The compound of clause 10, wherein $R^2$, $R^4$ and $R^6$ are —NH$_2$.

Clause 13: A pharmaceutical composition comprising an effective amount of the compound of any one of clauses 1-12, or a pharmaceutically acceptable salt thereof, and a pharmaceutically acceptable carrier.

Clause 14: A method of inhibiting amyloid-beta aggregation in a subject, comprising administering to the subject an effective amount of the compound of any one of clauses 1-12 or the pharmaceutical composition of clause 13.

Clause 15: A method of treating a Alzheimer's disease in a subject, comprising administering to the subject a therapeutically effective amount of the compound of any one of clauses 1-12 or the pharmaceutical composition of clause 13.

What is claimed is:

1. A compound of formula (I),

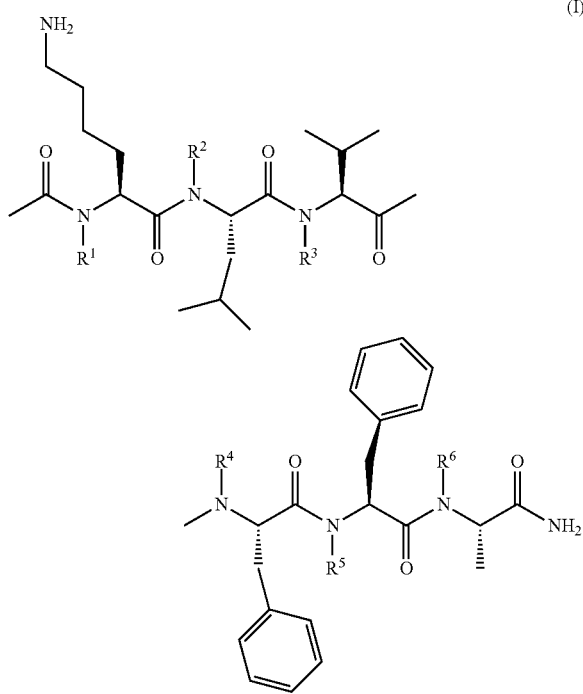

or a pharmaceutically acceptable salt thereof, wherein $R^1$, $R^2$, $R^3$, $R^4$, $R^5$, and $R^6$ are each independently selected from hydrogen or —$NH_2$, and wherein at least one of $R^1$, $R^2$, $R^3$, $R^4$, $R^5$, and $R^6$ is —$NH_2$.

2. The compound of claim 1, or a pharmaceutically acceptable salt thereof, wherein two of $R^1$, $R^2$, $R^3$, $R^4$, $R^5$, and $R^6$ are —$NH_2$.

3. The compound of claim 2, or a pharmaceutically acceptable salt thereof, wherein $R^1$ and $R^3$ are —$NH_2$.

4. The compound of claim 2, or a pharmaceutically acceptable salt thereof, wherein $R^1$ and $R^5$ are —$NH_2$.

5. The compound of claim 2, or a pharmaceutically acceptable salt thereof, wherein $R^2$ and $R^4$ are —$NH_2$.

6. The compound of claim 2, or a pharmaceutically acceptable salt thereof, wherein $R^2$ and $R^6$ are —$NH_2$.

7. The compound of claim 2, or a pharmaceutically acceptable salt thereof, wherein $R^3$ and $R^5$ are —$NH_2$.

8. The compound of claim 2, or a pharmaceutically acceptable salt thereof, wherein $R^4$ and $R^6$ are —$NH_2$.

9. The compound of claim 1, or a pharmaceutically acceptable salt thereof, wherein three of $R^1$, $R^2$, $R^3$, $R^4$, $R^5$, and $R^6$ are —$NH_2$.

10. The compound of claim 9, or a pharmaceutically acceptable salt thereof, wherein $R^1$, $R^3$ and $R^5$ are —$NH_2$.

11. The compound of claim 9, or a pharmaceutically acceptable salt thereof, wherein $R^2$, $R^4$ and $R^6$ are —$NH_2$.

12. A pharmaceutical composition comprising an effective amount of the compound of claim 1, or a pharmaceutically acceptable salt thereof, and a pharmaceutically acceptable carrier.

13. A method of inhibiting amyloid-beta aggregation in a subject, comprising administering to the subject an effective amount of the compound of claim 1, or a pharmaceutically acceptable salt thereof, or the pharmaceutical composition of claim 12.

14. A method of treating a Alzheimer's disease in a subject, comprising administering to the subject a therapeutically effective amount of the compound of claim 1, or a pharmaceutically acceptable salt thereof, or the pharmaceutical composition of claim 12.

* * * * *